United States Patent
D'Acosta et al.

(10) Patent No.: US 10,464,865 B2
(45) Date of Patent: *Nov. 5, 2019

(54) TREATING C8-C10 AROMATIC FEED STREAMS TO PREPARE AND RECOVER TRIMETHYLATED BENZENES

(71) Applicant: Swift Fuels, LLC, West Lafayette, IN (US)

(72) Inventors: Chris D'Acosta, West Lafayette, IN (US); Jeffery Miller, Naperville, IL (US); Robert Hoch, Hensonville, NY (US)

(73) Assignee: SWIFT FUELS, LLC, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/126,503

(22) Filed: Sep. 10, 2018

(65) Prior Publication Data

US 2019/0135716 A1 May 9, 2019

Related U.S. Application Data

(63) Continuation of application No. 15/871,678, filed on Jan. 15, 2018, now abandoned, which is a
(Continued)

(51) Int. Cl.
*C07C 6/06* (2006.01)
*C07C 15/02* (2006.01)
(Continued)

(52) U.S. Cl.
CPC .................. *C07C 6/06* (2013.01); *C07C 2/66* (2013.01); *C07C 4/18* (2013.01); *C07C 6/12* (2013.01);
(Continued)

(58) Field of Classification Search
CPC .. C07C 15/02; C07C 4/18; C07C 6/12; C07C 15/08; C07C 6/126; C07C 5/2732;
(Continued)

(56) References Cited

U.S. PATENT DOCUMENTS 2,593,561 A 4/1952 Herbst et al.
3,253,049 A 5/1966 Allen et al.
(Continued)

FOREIGN PATENT DOCUMENTS

CN 102 746 092 A 10/2012
JP 2002-226406 A 8/2002
(Continued)

OTHER PUBLICATIONS

Al-Khattaf, Sufaiman et al. "1,2,4-Trimethylbenzene Transformation Reaction Compared with its Transalkylation Reaction with Toulene over USY-Zeolite Catalyst," Chemical Eng, Dept., King Fahd Univ of Petroleum & Minerals, Dhahran, Saudi Arabia, Feb. 2007, pp. 1-29.
(Continued)

*Primary Examiner* — Sharon Pregler
(74) *Attorney, Agent, or Firm* — Woodard, Emhardt, Henry, Reeves & Wagner, LLP

(57) ABSTRACT

Methods are provided for the treatment of a feed stream containing C9 aromatic components to produce mesitylene-containing products. The methods include hydrodealkylating the feed stream to remove C2 and higher alkyl groups from the aromatic components and transalkylating the feed stream to rearrange the distribution of methyl groups among the aromatic components. Disclosed methods also include the treatment of a hydrocarbon feedstock by hydrodealkylation and/or transalkylation in order to produce a hydrocarbon product having an increased mass percentage of mesitylene.

33 Claims, 16 Drawing Sheets

Related U.S. Application Data continuation of application No. 14/256,589, filed on Apr. 18, 2014, now Pat. No. 9,890,095.

(60) Provisional application No. 61/813,333, filed on Apr. 18, 2013, provisional application No. 61/813,321, filed on Apr. 18, 2013.

(51) Int. Cl.
  *C07C 2/66* (2006.01)
  *C07C 4/18* (2006.01)
  *C07C 6/12* (2006.01)

(52) U.S. Cl.
  CPC .......... *C07C 15/02* (2013.01); *C07C 2529/08* (2013.01); *C07C 2529/18* (2013.01); *C07C 2529/40* (2013.01); *C07C 2529/70* (2013.01)

(58) Field of Classification Search
  CPC .......... C07C 2/66; C07C 5/2754; C07C 6/06; C07C 6/123; B01J 2229/26; B01J 2229/36; B01J 2229/42; B01J 27/13; B01J 29/26; B01J 29/7415; B01J 29/7469; B01J 29/7476
  See application file for complete search history.

(56) References Cited

U.S. PATENT DOCUMENTS

| | | |
|---|---|---|
| 3,260,764 A | 7/1966 | Kovach et al. |
| 3,412,521 A | 11/1968 | Bauman |
| 3,677,973 A | 7/1972 | Mitsche et al. |
| 4,172,813 A | 10/1979 | Feinstein et al. |
| 5,004,854 A | 4/1991 | Yan |
| 5,156,901 A | 10/1992 | Tanaka |
| 5,197,659 A | 3/1993 | Vassiliou |
| 5,285,957 A | 2/1994 | Halsell |
| 5,417,342 A | 5/1995 | Hutchison |
| 5,698,757 A | 12/1997 | Wu et al. |
| 5,702,053 A | 12/1997 | Kozakai |
| 5,799,861 A | 9/1998 | Bonner et al. |
| 6,079,617 A | 6/2000 | Kim |
| 6,136,155 A | 10/2000 | Berg |
| 6,138,903 A | 10/2000 | Baker |
| 6,189,330 B1 | 2/2001 | Retallick |
| 6,325,281 B1 | 12/2001 | Grogan |
| 6,536,654 B2 | 3/2003 | Reynolds |
| 7,094,192 B2 | 8/2006 | Schoenberger |
| 7,157,397 B2 | 1/2007 | Dalloro et al. |
| 7,229,677 B2 | 6/2007 | Miller |
| 8,049,048 B2 | 11/2011 | Rusek et al. |
| 9,890,095 B2 * | 2/2018 | D'Acosta ................. C07C 2/66 |
| 2002/0000297 A1 | 1/2002 | Kitano et al. |
| 2003/0226882 A1 | 12/2003 | Porchia et al. |
| 2005/0214512 A1 | 9/2005 | Fascio |
| 2005/0224501 A1 | 10/2005 | Folkert et al. |
| 2007/0000983 A1 | 1/2007 | Spurrell |
| 2007/0051782 A1 | 3/2007 | Lantz |
| 2008/0041860 A1 | 2/2008 | Wiedmeyer |
| 2008/0086982 A1 | 4/2008 | Parenteau |
| 2008/0087716 A1 | 4/2008 | Sadlier |
| 2008/0276643 A1 | 11/2008 | Heroux et al. |
| 2012/0067774 A1 | 3/2012 | Frey et al. |
| 2014/0316173 A1 | 10/2014 | Watermeyer De Wet et al. |
| 2014/0316174 A1 | 10/2014 | D'Acosta et al. |

FOREIGN PATENT DOCUMENTS

| | | |
|---|---|---|
| KR | 10-2012-0118272 A | 10/2012 |
| WO | WO 2008/073118 A1 | 6/2008 |

OTHER PUBLICATIONS

C. J. Egan, "Calculated Equilibria of the Methylbenzenes and Benzene from 298 Degrees to 1000 Degrees K." Journal of Chemical and Engineering Data, vol. 5, No. 3, Jul. 1960, pp. 298-299.
English Abstract of KR 1020120118272A to S-Oil Corporation, et al., Oct. 26, 2012.
Heinz Heinemann, Founding Editor, "Catalytic Naphtha Reforming" 2nd Edition, edited by GJ. Antos and A. M. Aitani, NY, Marcel Dekker, Inc. 2004, pp. 1-617.
International Search Report and Written Opinion issued in PCT/US2014/084681, dated Sep. 25, 2014, 11 pgs.
M. R. Rahimpour, et al., "Progress in catalytic naphtha reforming process: A review," Applied Energy, vol. 109, 2013, pp. 79-93.
S.A. Ali et al., "Conversion of heavy reformate into xylenes over mordenite-based catalysts," Chemical Eng. Research and Design, vol. 89, 2011, pp. 2125-2135.
English Abstract of CN 102 746 092A.
English translation of JP 2002-226406 Aug. 14, 2002 obtained by Lexis Nexis Total Patent on Nov. 29, 2018.
International Application PCT/US2018/012801 International Search Report and Written Opinion dated Mar. 6, 2018.

* cited by examiner

TREATING C8-C10 AROMATIC FEED STREAMS TO PREPARE AND RECOVER TRIMETHYLATED BENZENES

CROSS-REFERENCE TO RELATED APPLICATION

This application claims the benefit of U.S. patent application Ser. No. 15/871,678 filed Jan. 15, 2018 (7612-110), U.S. patent application Ser. No. 14/256,589 filed Apr. 18, 2014 (7612-46), U.S. Provisional Application No. 61/813, 321, filed Apr. 18, 2013 (7612-31), and U.S. Provisional Application No. 61/813,333, filed Apr. 18, 2013 (7612-32), each of which is hereby incorporated by reference.

FIELD OF THE INVENTION

The present invention relates to the preparation of mesitylene rich fuels and blending components from heavy aromatic feeds, particularly from C9 aromatic rich streams available from refineries.

BRIEF DESCRIPTION OF THE PRIOR ART

The refining industry currently formulates the motor gasoline pool from a wide range of hydrocarbon streams including $C_4$ to $C_{10}$ saturated branched acyclic alkanes and olefins and monocyclic aromatic compounds. However derived, these latter hydrocarbon streams contain a broad range of components and have usually been distilled, or otherwise treated (e.g., by solvent extraction), to obtain specific desired components or combinations of components. One purpose of these operations in the past has been to obtain high purity, often greater than 99%, chemical feed stocks such as para-xylene and benzene, which have been used in huge quantities in the manufacture of styrene, phenol, polyamide monomers, terephthalic acid and other chemical products. The streams resulting from the separation processes accordingly consist of product streams of benzene, toluene, $C_8$ aromatics containing xylenes, and a bottoms product of $C_9$ and $C_{10}$+ aromatics.

There is extensive knowledge in the refining industry regarding the use of catalysts to restructure molecules for the adaptation of these $C_4$-$C_{10}$ streams. However, these techniques do not satisfy the need for high octane fuels, particularly aviation fuels for piston and turbine engines, which have unique high octane, distillation and vapor pressure requirements. The prior art primarily has focused on fuels that are not able to meet the particularly higher motor octane demands of unleaded aviation fuel (MON≥102).

For example, U.S. Pat. No. 4,172,813 describes hydrodealkylation and transalkylation of fractionated heavy reformate to produce a high yield of xylenes by use of a tungsten/molybdenum catalyst. Further, a high yield of $C_2$-$C_4$ hydrocarbons is obtained as a result of the hydrodealkylation of the alkyl aromatics. More specifically, the '813 process involves reacting the $C_9$'s, separating the C6, C7, C8, trimethylbenzene and C10 reaction products, and then recycling the unreacted trimethylbenzenes. The goal of the process is to convert trimethyl benzenes ("TMB"'s) to xylenes, and particularly ethylbenzene-lean xylenes, as well as benzene and C2-C4 hydrocarbons. One can make additional C8 products by transferring methyl groups from one aromatic to another, e.g., from C9's and C10's to C6's and C7's. Under the same conditions, ethyl and propyl groups can be removed, i.e., by hydrodealkylation, forming ethane, propane, etc.

All the TMB isomers have a very similar boiling point. In the '813 patent, the unreacted TMB's are recycled to be converted to lighter aromatics. See '813 patent at column 8, lines 46-51.

The present invention uses a combination of processing steps to transform a typical mixed-C9 and higher aromatic rich feed stream such as might result from catalytic reforming. Catalytic reforming is frequently followed by a BTX (benzene, toluene, xylene) unit which recovers the light aromatics by extraction, distillation, or a combination of these processes. The aromatics cut left over after the BTX process is generally a C9 and higher aromatic feedstock which can be separated into specific, high octane C9 compounds and mixtures thereof which are isolated and recovered. While some of the individual processing methods have been known in the art, they have not been combined in the manner of the present invention.

It is an object of the present invention to provide methods for the efficient and cost effective production of 1,3,5-trimethyl benzene and pseudocumene fuel products from C9 aromatic feeds. It is a further object of the invention to provide such methods which further provide lower paraffins and C6-C8 aromatics as by-products.

A further object of the present invention is to provide TMB-rich fuel products, with or without pseudocumene, as fuels and fuel blending components.

SUMMARY OF THE INVENTION

This invention treats a $C_9$ aromatic blend feed stream to obtain a TMB-rich product. The process includes the hydrodealkylation (HDA) and transalkylation (TA) of the C9 feed to obtain the TMB-rich fraction. The process may also include further treatment to obtain a substantially pure mesitylene product and/or a mixed TMB product comprising mesitylene and pseudocumene. Recovery of other products may also be involved. The invention further comprises the TMB products of these processes. The invention thereby facilitates the preparation of an unexpectedly high octane aromatic stream, which can serve as a high-octane unleaded fuel or fuel blending component for a wide range of applications, particularly aviation gasoline and other high-performance transportation fuels. Further objects, features, aspects, benefits, advantages, and embodiments of the present invention will become apparent from the detailed description and drawings provided herewith.

DESCRIPTION OF SELECTED EMBODIMENTS

For the purpose of promoting an understanding of the principles of the invention, reference will now be made to the embodiments illustrated herein and specific language will be used to describe the same. It will nevertheless be understood that no limitation of the scope of the invention is thereby intended. Any alterations and further modifications of the described embodiments, and any further applications of the principles of the invention as described herein, are contemplated as would normally occur to one skilled in the art to which the invention relates. While certain aspects of the invention are shown in detail, it will be apparent to those skilled in the relevant art that some features that are not relevant to the present invention may not be shown for the sake of clarity.

The present invention provides a surprisingly efficient and cost effective method for the production of trimethyl benzenes, and particularly 1,3,5-trimethylbenzene (mesitylene), 1,2,4-trimethylbenzene (pseudocumene) and mixtures thereof. In a preferred embodiment, mesitylene is obtained as the primary component of a mesitylene/pseudocumene blend. In another preferred embodiment, mesitylene is obtained as an essentially pure component. These products may be used in a variety of ways, particularly as motor fuels or blending components, especially for aviation fuels.

Figure 1:
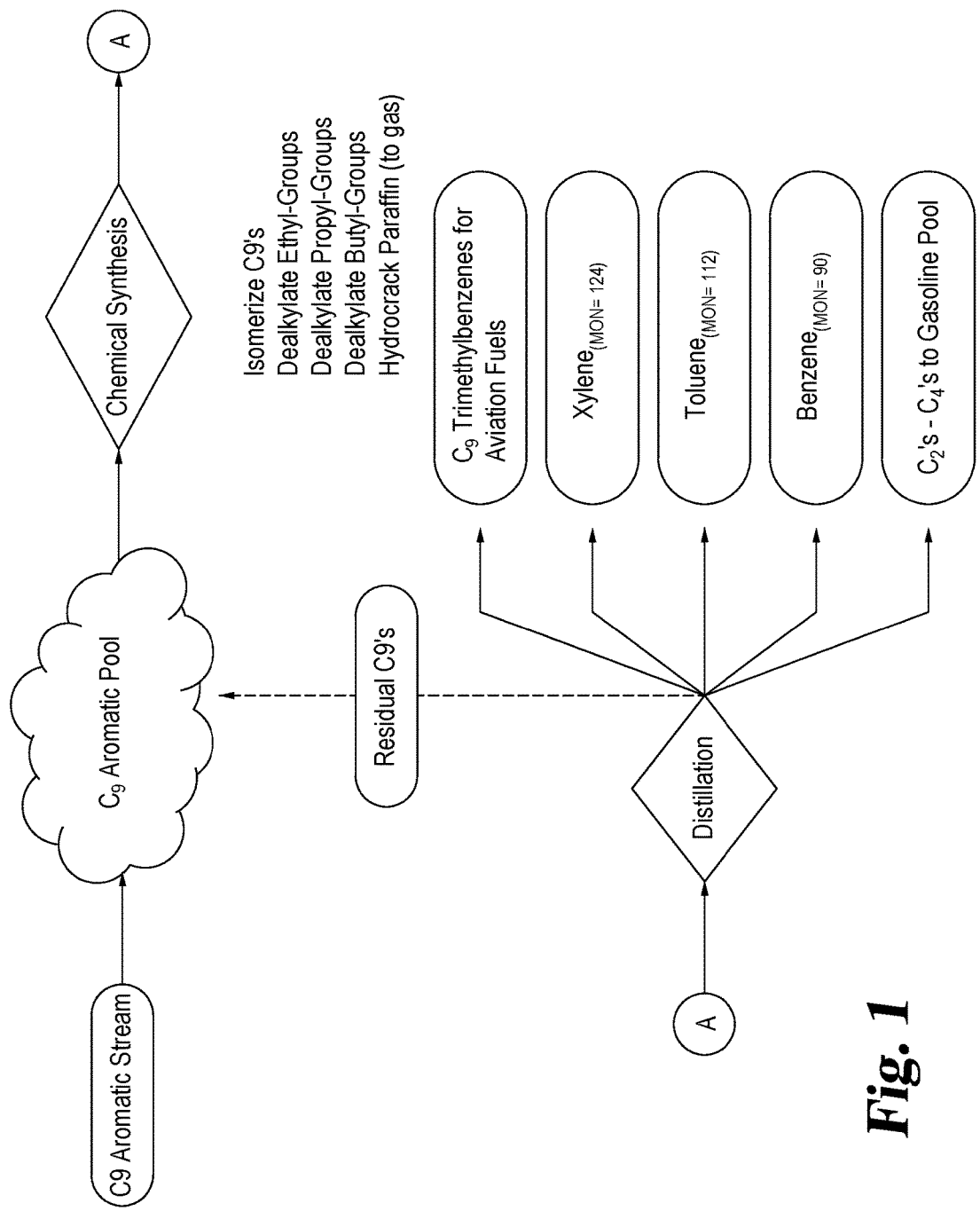
FIG. 1 is a diagrammatic view of a C9 Stream treatment process according to the present invention.

The Overall Process (FIG. 1)

The inventive process is directed to the treatment of feed streams which include C9 aromatics in combination with other components. As used herein, the term "C9 Stream" is intended to cover any available aromatic stream, including effluent refinery streams or fractions thereof, which includes a sufficient amount of C9 aromatics to make the process practical. One preferred C9 Stream is a catalytic naphtha reformer C9 effluent, particularly after BTX processing.

The C9 Stream may comprise specifically C9 aromatics, e.g., trimethyl-benzenes, ethyl-methyl-benzenes and propyl-benzenes. The stream may also comprise quantities of lower aromatics such as toluene, xylenes, ethylbenzene, etc. The C9 Stream may also include higher aromatics, such as diethylbenzenes, ethyl dimethyl benzenes, methyl propyl-benzenes, tetramethylbenzenes, pentamethylbenzene and various other alkyl benzenes. Of these, the present invention is directed to the preparation and collection of mesitylene, alone or in combination with pseudocumene. This provides a C9 aromatic product which has a much increased MON compared to the initial feed stream. As exemplified hereafter, for example, the present invention can convert a C9 aromatic feed stream having a MON in the order of 100, to a C9 product having a MON of 111. The result of the present invention is therefore a product which is useful itself as a motor fuel, an aviation fuel, of high octane, and/or which may be used to blend with gasoline or other components to provide fuels of various octanes as desired.

As shown in FIG. 1, the inventive process starts with a C9 Stream which is chemically treated, alone or in combination with recycle or other feed streams. The treatments provide hydrodealkylation of ethyl, propyl and butyl groups, and transalkylation and isomerization of the C9's, to yield an effluent "A". This process is followed by one or more steps which treat the "A" stream to allow separate collection of the desired C9 trimethylbenzene products. These further separation steps may also provide for the separate collection of xylenes, toluenes, benzene, light hydrocarbons, and hydrogen. The overall process provides a suitable yield of the desired trimethylbenzene products, as well as providing various other product streams that have value in gasolines and for other products and purposes.

C9 Aromatic Feed Streams

In the simplest form of the invention, the C9 Stream contains primarily C9 and higher components, and the process involves several steps for converting the C9 components to mesitylene and pseudocumene, particularly mesitylene. However, while a high concentration of C9 aromatics in the feed stream may be preferred, it will be appreciated that the C9 feed may also include a variety of C7-C12 components. Examples of typical feed streams are provided elsewhere herein. The present invention applies a number of processes which convert these various components of a C9 feed stream to a desirably high yield of the desired mesitylene and pseudocumene.

One process is hydrodealkylation, which selectively removes the ethyl and propyl constituents of the aromatics, while leaving the methyl constituents. A second process is isomerization, which is performed, for example, to convert 1,2,3-trimethyl benzene to the desired mesitylene and pseudocumene. Conversion to mesitylene, and/or pseudocumene, may also occur for the hydrodealkylated C9 components. Thus, a third reaction which may occur is transalkylation, which is the reaction of light (C7 and C8) and heavy methylbenzenes, i.e., C10, C11 or C12, into trimethylbenzenes, including pseudocumene and mesitylene. Optionally, saturated hydrocarbons that may be present in the feed stream will be hydrocracked into lower alkanes, which are separated by distillation.

A significant advantage of the present invention is that it is operable with aromatic feeds which are readily available, for example from catalytic reforming of heavy naphtha. A number of proprietary catalytic reforming processes are available, but they possess many features in common. The purpose of catalytic reforming is to increase the octane number of a refinery stream, primarily by converting the naphthenes to aromatics and the paraffins to more branched structures. Typically feed stocks are rich in paraffins and naphthenes with some aromatic content and product streams are somewhat reduced in paraffin content, but significantly reduced in naphthenes. Aromatics are usually the largest component of catalytic reformate. Depending on the refinery and the feed stocks available, different degrees of reaction severity may be chosen. In general the higher the severity, the higher the aromatic content and the lower the paraffin content of the effluent.

Although catalytic reforming is a net hydrogen producer, some hydrogen is typically recycled to the feed to help minimize coking. Reactors are typically fixed bed units. The net reaction is endothermic. Heat is supplied by a process furnace. There may be multiple passes through the furnace and multiple separate catalyst beds.

Although catalytic reforming processes differ in the catalyst formulations used, all current processes use precious Pt group metals. Because precious metal catalysts are subject to poisoning, feed to catalytic reforming is typically treated to remove sulfur compounds and other catalyst poisons. Operation may be described as continuous, cyclic or regenerative; these terms are descriptive of equipment configurations designed to permit replacement and/or regeneration of catalyst without complete unit shutdown. This is an important consideration because reforming catalysts tend to become fouled over time by the deposition of coke, although they can be regenerated by oxidation. A fuller discussion of catalytic reforming can be found in Antos, G. J. and Aitani, A. M., "Catalytic Naphtha Reforming" Marcel Dekker. (2004) and Rahimpour, M. R. et al., Applied Energy, v109, pages 79-93 (2013) "Progress in Catalytic Naphtha Reforming Process: A Review".

Such feeds are the result of the typical naphtha reformate process, for example, and may include a variety of other aromatic components, as well as non-aromatic components such as alkanes. Typical refinery C9 fractions may include a variety of C7-C10 components. For example, heavy reformate typically contains significant amounts of C10 and higher aromatics. Heavy reformate may be treated by distillation to remove the C10's and heavier components, yielding "fractionated heavy reformate." Benzene, toluenes and xylenes may be removed through a conventional BTX process, which sometimes has already been carried out by the refinery before the C9 fraction is isolated. The concentration of C9 aromatics in the feed will depend on the processing of the feed prior to its use in the present invention.

It is a significant advantage of the present invention that the process uniquely combines several types of treatments which effectively eliminate or convert these various feed streams to the desired C9 product(s) in high proportion.

Table 1 lists typical constituents of a heavy reformate feed useful with the present invention.

TABLE 1

Composition of heavy reformate feedstock.

| Major compound | Short name | wt. % |
| --- | --- | --- |
| Iso-propyl benzene | iPB | 1.7 |
| n-Propyl benzene | nPB | 4.3 |
| 1-Methyl 2-ethyl benzene | 1M2EB | 6.5 |
| 1-Methyl 3-ethyl benzene | 1M3EB | 18.5 |
| 1-Methyl 4-ethyl benzene | 1M4EB | 9.1 |
| 1,2,3-Tri-methyl benzene | 123TMB | 6.6 |
| 1,2,4-Tri-methyl benzene | 124TMB | 39.1 |
| 1,3,5-Tri-methyl benzene | 135TMB | 10.1 |
| Total $A_9$ | | 95.9 |
| n-Butyl benzene | nBB | 0.5 |
| 1,4-Diethyl benzene | 14DEB | 0.8 |
| 1,3-Diethyl benzene | 13DEB | 0.4 |
| 1,3-Dimethyl, 5-ethyl benzene | 13DM5EB | 0.8 |
| 1,4-Dimethyl, 2-ethyl benzene | 14DM2EB | 0.4 |
| Others $A_{10}$ | | 1.2 |
| Total $A_{10}$ | | 4.1 |

Process Components

HDA

The present invention includes the steps of aromatic hydrodealkylation (HDA) of certain aromatic compounds that may be present in the C9 aromatic feed. The process is carried out under conditions which do not cleave the substituent methyl groups, but will selectively remove the higher C2-C4 alkyl substituents, as their corresponding alkanes, thus converting the higher (C2+) alkyl benzenes to leave only a mix of benzene and methylated benzenes as the aromatic constituents. For example, ethyl toluene is converted to ethane and toluene, propyl benzene is converted to propane and benzene, and butyl benzene (a C10 compound) is converted to butane and benzene. The consequence of the HDA process is therefore the production of, inter alia, benzene, toluene and polymethyl benzenes, including xylenes, as well as certain lower alkanes.

TA

The transalkylation (TA) and isomerization step results in a redistribution of methyl groups among the aromatics. Any of the C6-C10 aromatics may be affected by TA. Thus, a C8 aromatic may add a methyl group or a C10 may give up a methyl group—each resulting in formation of a TMB. The present invention combines HDA and TA with correlated recycle and recovery steps to obtain a high yield of mesitylene.

One aspect of this process, therefore, involves taking advantage of the known equilibrium distribution of trimethyl benzenes in an aromatic pool. Egan describes aspects of the equilibrium distribution of methylbenzenes in transalkylation. See Egan, Clark J., "Calculated Equilibria of the Methylbenzenes and Benzene from 298° to 1000° K", J. Chem. And Eng. Data 5 (3) 298, July 1960, hereby incorporated by reference in its entirety. The present process includes selectively recovering the mesitylene, by itself or optionally with the pseudocumene, from the equilibrium pool of the C9 and other isomers.

As known in the art, a relevant parameter in transalkylation is the ratio in the feed stream of methyl groups to benzene groups. Egan shows, for example, that the equilibrium mesitylene concentration (as well as the pseudocumene concentration) peaks at a methyl/benzene ratio of 3.0. It is therefore a preferred embodiment of the present invention, though not a requirement, to operate the transalkylation step with a methyl/benzene ratio of the feed close to 3.0. This is readily accomplished, for example, by recycling tetra and higher methylbenzenes. Note that these higher alkylbenzenes need only be present at the final transalkylation step and need not flow through the multi-stage hydrodealkylation system.

Sample HDA/TA Processes

The HDA/TA process is generally understood in the art. It provides for the removal of C2 and higher alkyl groups from the aromatics of the C9 Stream, and an equilibrium distribution of the methyl groups among the aromatics. An example of a conventional combined HDA/TA process is described in detail in U.S. Pat. No. 4,172,813, which is hereby incorporated by reference in its entirety. As described in the '813 patent, for example, the feed is contacted with a suitable catalyst in the presence of a hydrogen-affording gas. The '813 patent describes a TMB stream which is an equilibrium mixture of C9 methyl aromatics with essentially all higher alkyl groups removed. The feed stock contained 65% toluene with the balance C9 and higher aromatics. Close to equilibrium results are obtained at 800-900° F. and 172 PSIG at a WHSV of 3.7 or 3.8 $hr^{-1}$. Excess hydrogen for the dealkylation reaction was provided; the examples use just over 6:1 of H2:hydrocarbon. Various operating conditions are selected to suit the catalyst, which may include particular molar ratios of hydrogen to hydrocarbon, not including inert, gas phase hydrocarbons. Operating pressures, temperatures and contact times are also selected in accordance with known operation of these types of catalysts.

Catalysts

An example of a suitable catalyst is a metal and zeolite operated at temperatures from 200-1000° C., pressures from 1-100 atmospheres and a space velocity from 0.1-10 $hr^{-1}$. The catalyst metals include, Pt, Pd, Re, Rh, Ir and Mo. These may be present as an oxide, metallic or alloy nano-particles. The preferred metals are Pt, Re and Mo. The metal loadings can be from 0.05 to about 10 weight % as metal in the catalyst. The metals are typically supported on a high surface area support such as alumina, silica, and other refractory oxides. These oxides provide high surface area, porosity and physical strength. The oxide support also contains an acidic form of zeolite Y (FAU), beta (BEA), mordenite (MOR), ZSM-5 (MFI). The amount of zeolite may be from about 10% to 90% of the oxide support. For C9 aromatic feeds, large pore zeolites are preferred, including zeolite Y (FAU), mordenite (MOR) and beta (BEA).

The combined process of HDA and TA thus treats the C9 components in a manner to increase the proportion of desired mesitylene and pseudocumene, while converting other likely present components to readily eliminated compounds. Hemimellitene, 1,2,3, trimethylbenzene, is the most difficult component to separate by distillation from mesitylene and pseudocumene. Fortunately, as shown by Egan, the equilibrium concentration of hemimellitene is always quite low. The ethyl toluenes which have a boiling point close to that of mesitylene are eliminated by removing the ethyl groups in the HDA process. Unlike ethyl toluenes, the boiling point of toluene is sufficiently different that it is readily separated from mesitylene (and pseudocumene) by distillation. As a result, all components present following the HDA/TA processes are readily separated from the mesitylene and pseudocumene. For example, the benzene, toluenes and xylenes, if not converted to the desired trimethyl benzenes, can be removed through a conventional BTX tower. The lower alkanes and hydrogen are easily separated in a conventional manner prior to the BTX tower, and could even be removed prior to the TA unit when operated separately from the HDA reactors.

Hydrocracking

As has been previously described, many refineries practice high severity catalytic reforming and follow this operation with what is known in the art as a BTX extraction unit to recover the light aromatics valuable as chemical feed stocks. In this scenario, the reformer effluent contains a relatively low concentration of light paraffins which are conveniently removed prior to the BTX unit. BTX raffinate is heavy aromatics suitable for feed to the present invention.

If a significant amount of paraffins are present in the C9 Stream, the process preferably includes the step of hydrocracking. Hydrocracking is well known in the art and occurs under the same reactions conditions as HDA and TA. Alkanes and cycloalkanes are cracked into lower molecular weight alkanes, which are separated by distillation.

BTX

Table 2 provides a typical effluent composition from a low severity catalytic reformer. This stream may be fed directly into the process of the present invention. The paraffin components will pass through both the HDA and TA reactors unreacted. Transalkylation effluent can then conveniently be fed to a BTX unit whose raffinate will be a mixture of C9 and higher methyl aromatics. A pseudocumene/mesitylene mixture is readily recovered from this stream (and can be further processed to obtain pure mesitylene), leaving a higher aromatics stream suitable for recycle to transalkylation.

TABLE 2

| | |
|---|---|
| C5 paraffin | 0.272 |
| C6 paraffin | 0.04 |
| C7 paraffin | 0.041 |
| C8 paraffin | 0.053 |
| C9 paraffin | 0.033 |
| C10 paraffin | 0.007 |
| Naphthenes | 0.01 |
| Benzene | 0.009 |
| Toluene | 0.136 |
| C8 aromatics | 0.274 |
| C9 aromatics | 0.126 |
| Total | 1.001 |

Alternatively, if the hydrodealkylation and transalkylation reactions are carried out in separate reactors, the BTX unit can be positioned between the HDA and TA steps. In this case, a simple BTX distillation can remove C6-C8 components formed in TA. As above, a pseudocumene/mesitylene mixture can be recovered by distillation and the heavier aromatics can be recycled.

Many commercial proprietary BTX extraction systems are available and are known by trade names such as Udex and Tetra. Solvents such as higher ethylene or propylene glycols or sulfolane are employed. Any of these systems are suitable for use as above described.

Figure 2:
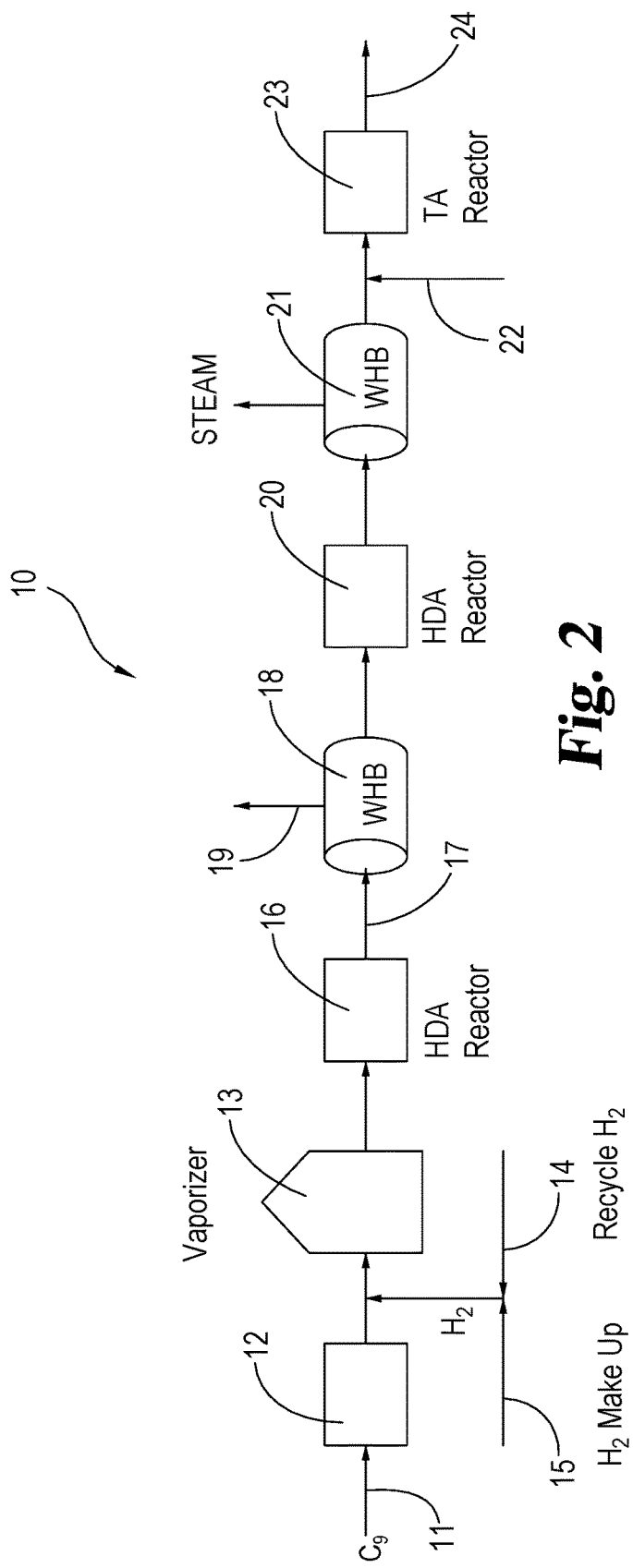
FIG. 2 is a flow diagram showing typical major components of a process according to an embodiment of the present invention.
Figure 3:
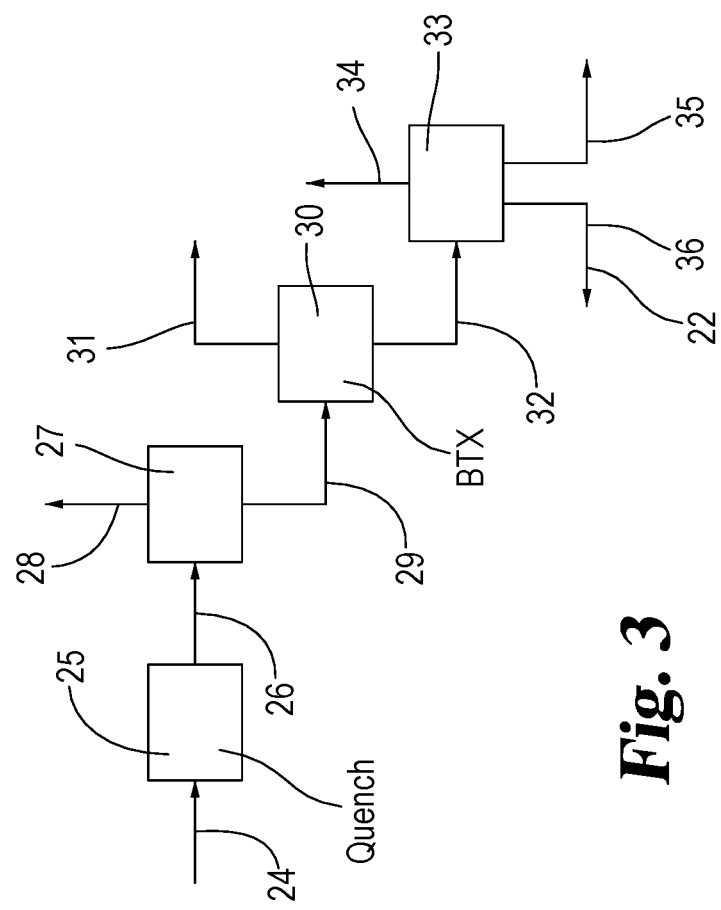
FIG. 3 is a flow diagram identifying further processing components, steps and products of the present invention.

The Process in Detail (FIGS. 2-3)

The present invention is shown diagrammatically in FIG. 1. This diagram indicates the overall process involving the HDA and TA processes, combined with recycle of certain components, which increase the concentration of mesitylene over that present in the initial C9 Stream. This process generally involves several conventional steps which are combined in a unique manner, with other process methodology, to produce a product which is rich in TMB. A more specific exemplary process is described hereafter, but it will be appreciated that certain aspects of the described process may be varied as understood by those skilled in the art. For example, the following description provides separate HDA and TA reactors, but it is within the skill in the art to operate such reactors so as to achieve concurrent HDA and TA within individual reactors.

Referring to FIG. 2, there is shown a preferred embodiment of a process 10 according to the present invention. In general, the feed stock is treated using one or more adiabatic reactors operating at conditions to perform the HDA/TA processes, as generally known. The use of multiple reactors, with intermediate heat removal to steam, facilitates control of the exothermic HDA reactions. HDA can also be carried out in an isothermal reactor wherein the catalyst is contained in tubes and a heat transfer fluid on the shell side removes the heat. Typical heat transfer fluids are Dowtherm and other heat transfer oils or high pressure steam. It is also well known in the art to place the catalyst on the shell side of an isothermal reactor and the heat transfer fluid in the tubes. Cold shot cooling can also be employed. In this embodiment, instead of recovering the heat to steam in between reactor stages, additional cold hydrogen or other inert gas or liquid component is added between stages.

Typically, the C9 Stream is mixed with a hydrogen-containing gas and preheated to a suitable temperature, and then transferred to the hydrodealkylation/transalkylation reaction zone. Besides being a reactant, the hydrogen also provides dilution of the hydrocarbon stream and limits the adiabatic temperature rise across each reaction stage. It will be clear to one of skill in the art that the hydrogen can be replaced in part (only in part because the hydrogen is reactant as well as diluent) by a gas inert in the reaction such as nitrogen or a lower hydrocarbon such as methane, ethane or propane or mixtures thereof or mixtures thereof further comprising hydrogen or nitrogen. As shown in FIG. 2, the C9 Stream 11 is provided to booster pump 12 which elevates the liquid to a reaction pressure, e.g., 400 PSIA, before the stream enters vaporization furnace 13. Hydrogen recycle 14 is combined with make-up hydrogen 15 and passes through a separate coil in furnace 13. These gas phase streams combine before entering the first stage reactor 16. Effluent 17 enters a waste heat boiler 18 where it is cooled by generating 750 PSI steam 19. A second stage reactor 20 and boiler 21 are preferably included, and one or more additional stages (not shown) may be added. In this embodiment, effluent from the last of the HDA stages is mixed with a C9 and higher aromatics recycle stream 22 (from a subsequent separation section) before being fed to a transalkylation reactor 23, which yields effluent stream 24.

As shown in FIG. 3, the effluent 24 from the HDA/TA reactor(s) is fed to a quench column 25 which cools the material. This cooled material is then fed through line 26 to a partial condensation unit 27. The lighter components comprising C2-C4 paraffins and hydrogen are removed by way of line 28 and the heavier components comprising C6-C10 and higher aromatics are removed through line 29. Alternatively, the quench column overheads can be fed to an absorption or extraction unit to separate the hydrogen from the light hydrocarbons. The heavier components in line 29 are then fed into a conventional type BTX (benzene/toluene/xylene) column 30. The BTX column separates out the toluenes, xylenes, and benzene (31) from the C9 and higher aromatics.

The bottoms 32 from the BTX column pass to the product column 33 which takes the desired mesitylene/pseudocumene product overhead 34 from a bottoms including some pseudocumene and higher polymethylbenzenes. Pseudocumene distributes between the overheads and bottoms of this column. A purge 35 of C10 and higher aromatics is taken form the bottoms of this column to prevent unreactive heavy compounds from building up. The balance 36 of the higher polymethylbenzenes is recycled to the transalkylation unit by way of line 22 (FIG. 2).

The lighter component overheads 28 from quench column 27 may also be processed for recovery of the lighter components. Most of the $C_3$ and $C_4$ is removed against cooling water and the residual gasses pass to an ethane chiller (not shown) where the ethane is condensed against chilled brine at about −5° C. Uncondensed hydrogen is recompressed to reaction pressure and recycled through line 14 (FIG. 2).

This process yields a TMB-rich product containing primarily mesitylene (1,3,5-trimethyl benzene), and some amount of pseudocumene. As used herein, the term "TMB-rich" refers to a C9 aromatic product containing at least about 50 wt % mesitylene, preferably at least 60 wt % mesitylene and more preferably at least 70 wt % mesitylene. The TMB-rich product is well suited for use as a motor fuel, especially an aviation fuel, either as it is obtained or after blending with other components. In particular, the presence of the mesitylene provides a desirably high MON and other characteristics suitable for such fuels. It is an additional advantage of the present invention that the inventive process provides TMB-rich products which have this utility in the absence of TEL and aromatic amines.

The process may optionally include a further purification of the TMB-rich product to obtain a Substantially Pure Mesitylene product, which refers to a product that is at least about 90 wt % mesitylene, and preferably at least 95 wt % mesitylene. To obtain a Substantially Pure Mesitylene product, an additional column is used to resolve the pseudocumene and mesitylene. In one approach, for example, a column is included which is used to take an overhead pseudocumene composition as 98 wt %. However, it will be found that in most instances the TMB-rich product is sufficient and has excellent utility as a fuel or fuel blending component, without requiring the additional steps required to obtain a Substantially Pure Mesitylene product.

Auxiliary equipment, such as pumps and heat exchangers, are not shown in the drawings. Such auxiliary equipment is well-known and the uses and locations of this equipment in this process system will be recognized easily by those having ordinary skill in the art.

Mention Combining of HDA and TA.

Further embodiments and aspects of the process of the present invention may be found in the following examples.

These embodiments and examples are presented for purposes of illustration only and are not intended to limit the scope of the invention.

Example 1

The present invention is useful with a variety of C9 aromatic streams, including those obtained directly from a reformer. By way of example, a C9 stream from catalytic reforming was analyzed for chemical composition and was found to contain the components as set forth in Table 2.

TABLE 3

Reformate Sample ($C_8$, $C_9$ & $C_{10}$ Aromatic Stream)

| | | |
|---|---|---|
| 95-63-6 | 1,2,4-trimethyl-benzene | 38.174% |
| 611-14-3 | 1-ethyl-2-methyl-benzene | 17.316% |
| 622-96-8 | 1-ethyl-4-methyl-benzene | 8.537% |
| 526-73-8 | 1,2,3-trimethyl-benzene | 7.280% |
| 108-67-8 | 1,3,5-trimethyl-benzene | 5.520% |
| 108-38-3 | 1,3-dimethyl-benzene | 3.097% |
| 141-93-5 | 1,3-diethyl-benzene | 2.779% |
| 873-49-4 | cyclopropyl-benzene | 2.088% |
| 2870-04-4 | 2-ethyl-1,3-dimethyl-benzene | 2.036% |
| 1074-43-7 | 1-methyl-3-propyl-benzene | 1.561% |
| 933-98-2 | 1-ethyl-2,3-dimethyl-benzene | 1.230% |
| 95-93-2 | 1,2,4,5-tetramethyl-benzene | 1.050% |
| 874-41-9 | 1-ethyl-2,4-dimethyl-benzene | 1.011% |
| 103-65-1 | propyl-benzene | 0.915% |
| 95-93-2 | 1,2,4,5-tetramethyl-benzene | 0.715% |
| 535-77-3 | m-Cymene | 0.697% |
| 135-98-8 | S-Butyl-benzene | 0.657% |
| 488-23-3 | 1,2,3,4-tetramethyl-benzene | 0.479% |
| 934-80-5 | 4-ethyl-1,2-dimethyl-benzene | 0.396% |
| 106-42-3 | P-Xylene | 0.319% |
| 91-20-3 | Napthalene | 0.267% |
| 135-98-8 | S-Butyl-benzene | 0.250% |
| 104-51-8 | butyl-benzene | 0.224% |
| 2870-04-4 | 2-ethyl-1,3-dimethyl-benzene | 0.201% |
| 135-01-3 | 1,2-diethyl-benzene | 0.162% |
| 768-49-0 | (2-methyl-1-propenyl)-benzene | 0.149% |
| | Unknown | 2.890% |
| | | 100.000% |

After processing in accordance with the present invention, including hydrodealkylation and transalkylation/isomerization, the resulting mixture of tri-methyl C9-aromatics produces products as shown in Table 3. Table 3 highlights specifically how this invention separates the various compounds via hydrodealkylation of the ethyl and propyl groups resulting in ethane, propane, benzene, toluene and xylene, and isomerization of the methyl benzenes, yielding the trimethyl benzenes. Referring to Table 3, it is shown, for example, that 1-ethyl-2-methyl-benzene yields ethane and toluene, and 1,3-diethyl-benzene is broken down to ethane and benzene.

TABLE 4

DEALKYLATION SNYTHESIS -- FOR DISTILLATION

| $C_2H_6$ Ethane | $C_3H_8$ Propane | n-$C_4H_{10}$ Butane | i-$C_4H_{10}$ Isobutane | $C_6C_6$ Benzene | $C_7H_8$ Toluene | $C_8H_{10}$ Xylene |
|---|---|---|---|---|---|---|
| X | | | | | X | |
| X | | | | | X | |
| | | | | | | X |
| X | | | | X | | |
| | X | | | X | | |
| X | | | | | | X |
| | X | | | | X | |
| | | | | | X | X |

TABLE 4-continued

DEALKYLATION SNYTHESIS -- FOR DISTILLATION

| X | | | | | X | | |
|---|---|---|---|---|---|---|---|
| | X | | | X | | | |
| | | | X | X | | | |
| X | | | | | | X | |
| | | | | | | X | |
| | | X | X | | | | |
| | X | | X | | | | |
| X | | | | | X | | |
| X | | | X | | | | |
| | X | | | | X | | |
| −89° C. | −42° C. | −1° C. | −9° C. | 80° C. | 111° C. | 135° C. | |

Typical Boiling Points

Reformate Sample ($C_8$, $C_9$ & $C_{10}$ Aromatic Stream)

| 95-63-6 | 1,2,4-trimethyl-benzene | 38.174% |
|---|---|---|
| 611-14-3 | 1-ethyl-2-methyl-benzene | 17.316% |
| 622-96-8 | 1-ethyl-4-methyl-benzene | 8.537% |
| 526-73-8 | 1,2,3-trimethyl-benzene | 7.280% |
| 108-67-8 | 1,3,5-trimethyl-benzene | 5.520% |
| 108-38-3 | 1,3-dimethyl-benzene | 3.097% |
| 141-93-5 | 1,3-diethyl-benzene | 2.779% |
| 873-49-4 | cyclopropyl-benzene | 2.088% |
| 2870-04-4 | 2-ethyl-1,3-dimethyl-benzene | 2.036% |
| 1074-43-7 | 1-methyl-3-propyl-benzene | 1.561% |
| 933-98-2 | 1-ethyl-2,3-dimethyl-benzene | 1.230% |
| 95-93-2 | 1,2,4,5-tetramethyl-benzene | 1.050% |
| 874-41-9 | 1-ethyl-2,4-dimethyl-benzene | 1.011% |
| 103-65-1 | propyl-benzene | 0.915% |
| 95-93-2 | 1,2,4,5-tetramethyl-benzene | 0.715% |
| 536-77-3 | m-Cymene | 0.697% |
| 135-77-3 | S-Butyl-benzene | 0.657% |
| 488-23-3 | 1,2,3,4-tetramethyl-benzene | 0.479% |
| 934-80-5 | 4-ethyl-1,2-dimethyl-benzene | 0.396% |
| 106-42-3 | P-Xylene | 0.319% |
| 91-20-3 | Napthalene | 0.267% |
| 135-98-8 | S-Butyl-benzene | 0.250% |
| 104-51-8 | butyl-benzene | 0.224% |
| 2870-04-4 | 2-ethyl-1,3-dimethyl-benzene | 0.201% |
| 135-01-3 | 1,2-diethyl-benzene | 0.162% |
| 768-49-0 | (2-methyl-1-propenyl)-benzene | 0.149% |
| | Unknown | 2.890% |
| | | 100.000% |

Following processing in accordance with the present invention, an initial feed is converted as follows (based on vol %):

TABLE 5

| | Prior to Processing | After Processing |
|---|---|---|
| Mesitylene | 7.37% | 24.61% |
| Pseudocumene | 37.52% | 11.94% |
| Mixed C9's/C10's+ | 50.60% | 9.62% |
| Mixed-Xylenes | 4.51% | 38.71% |
| Toluene | 0 | 6.75% |

Figure 4:
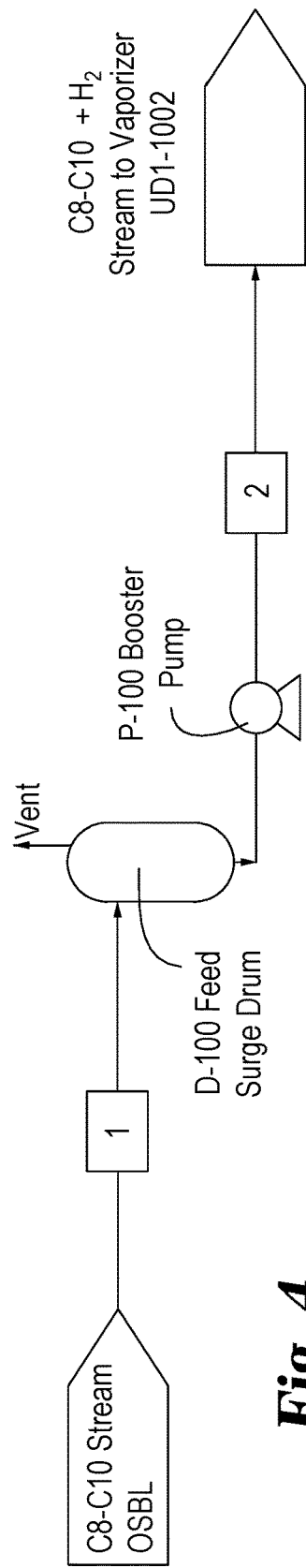
FIGS. 4-16 are diagrams showing various portions of an overall process in accordance with the present invention.
Figure 5:
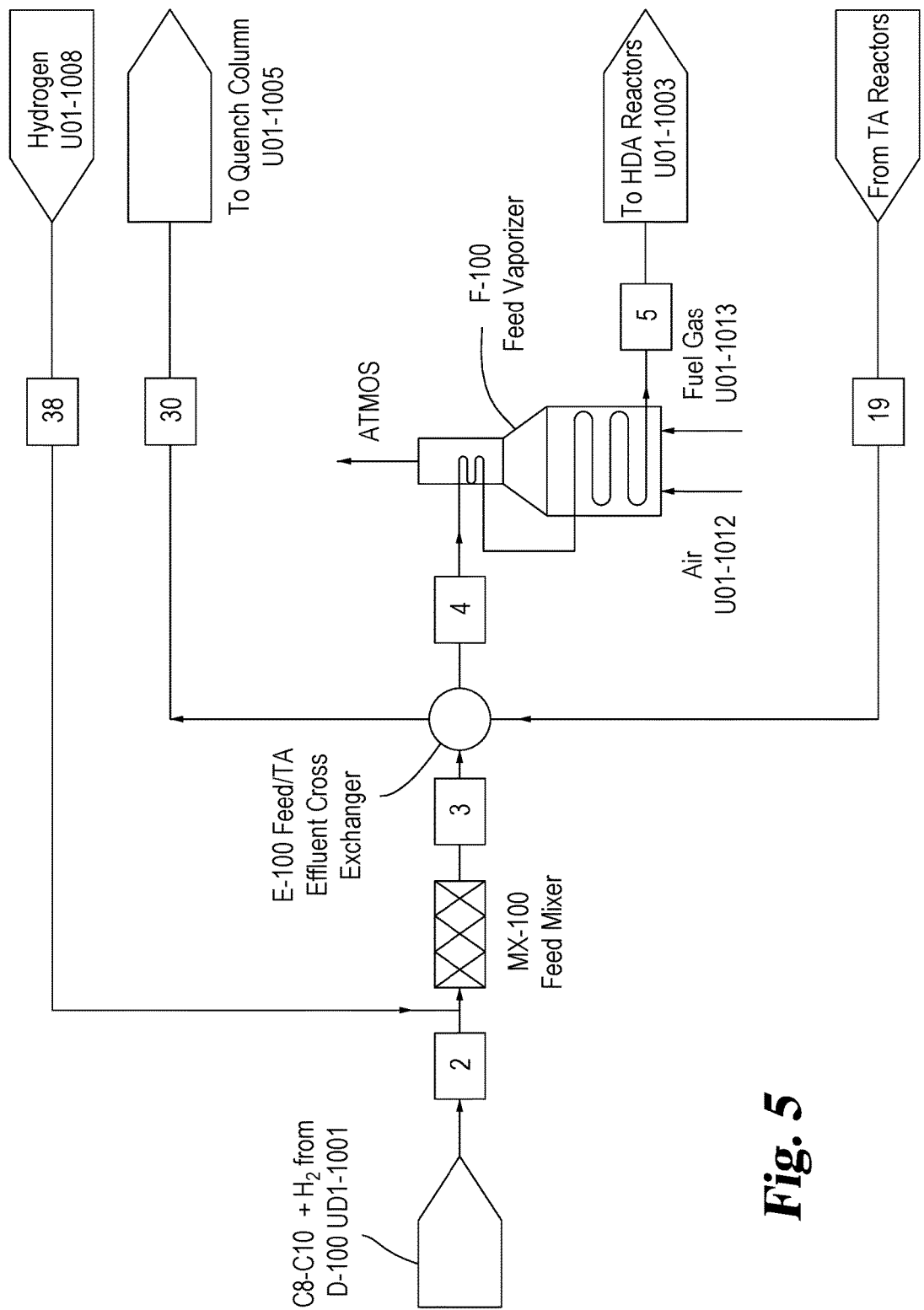
Figure 6:
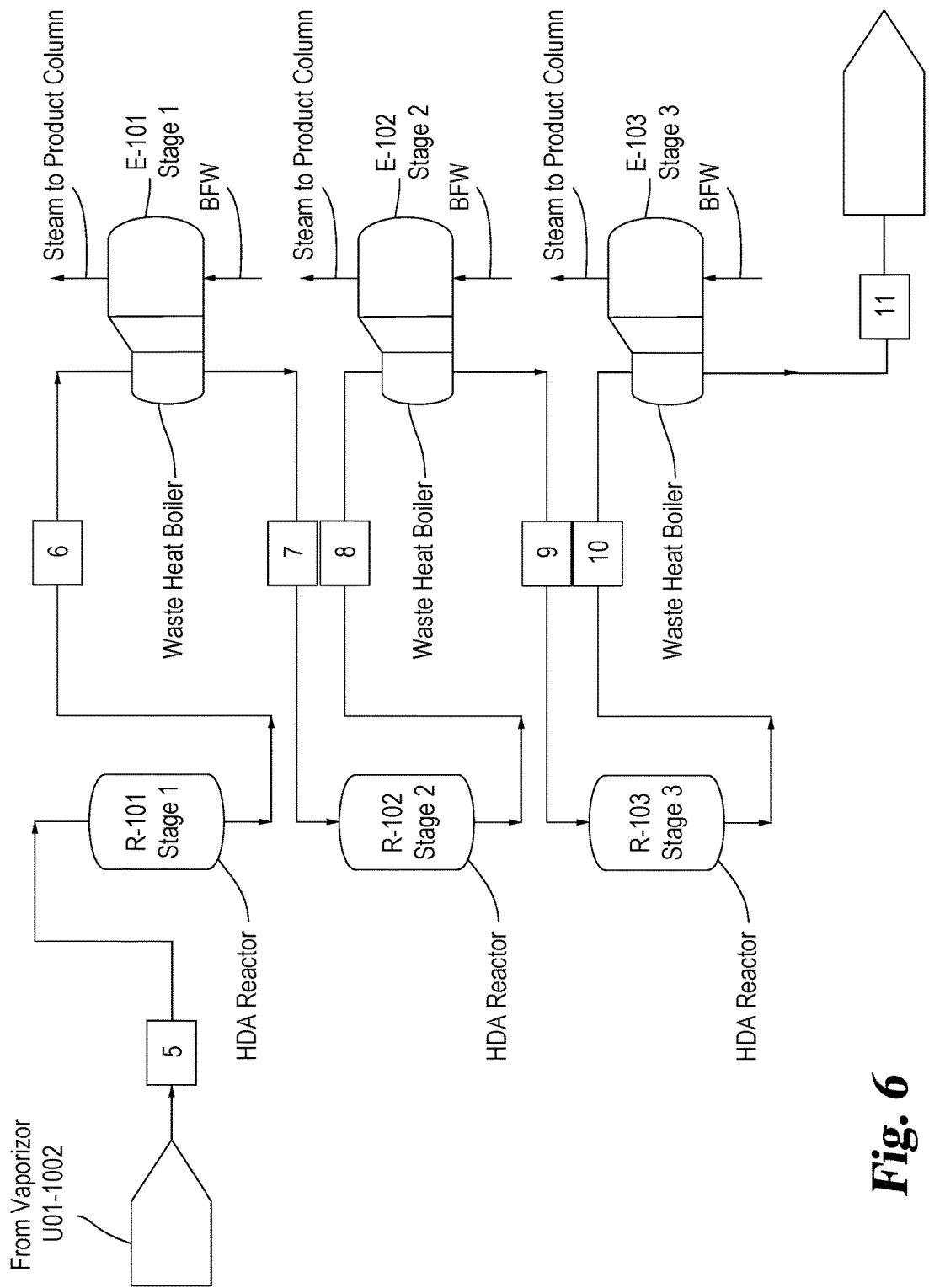
Figure 7:
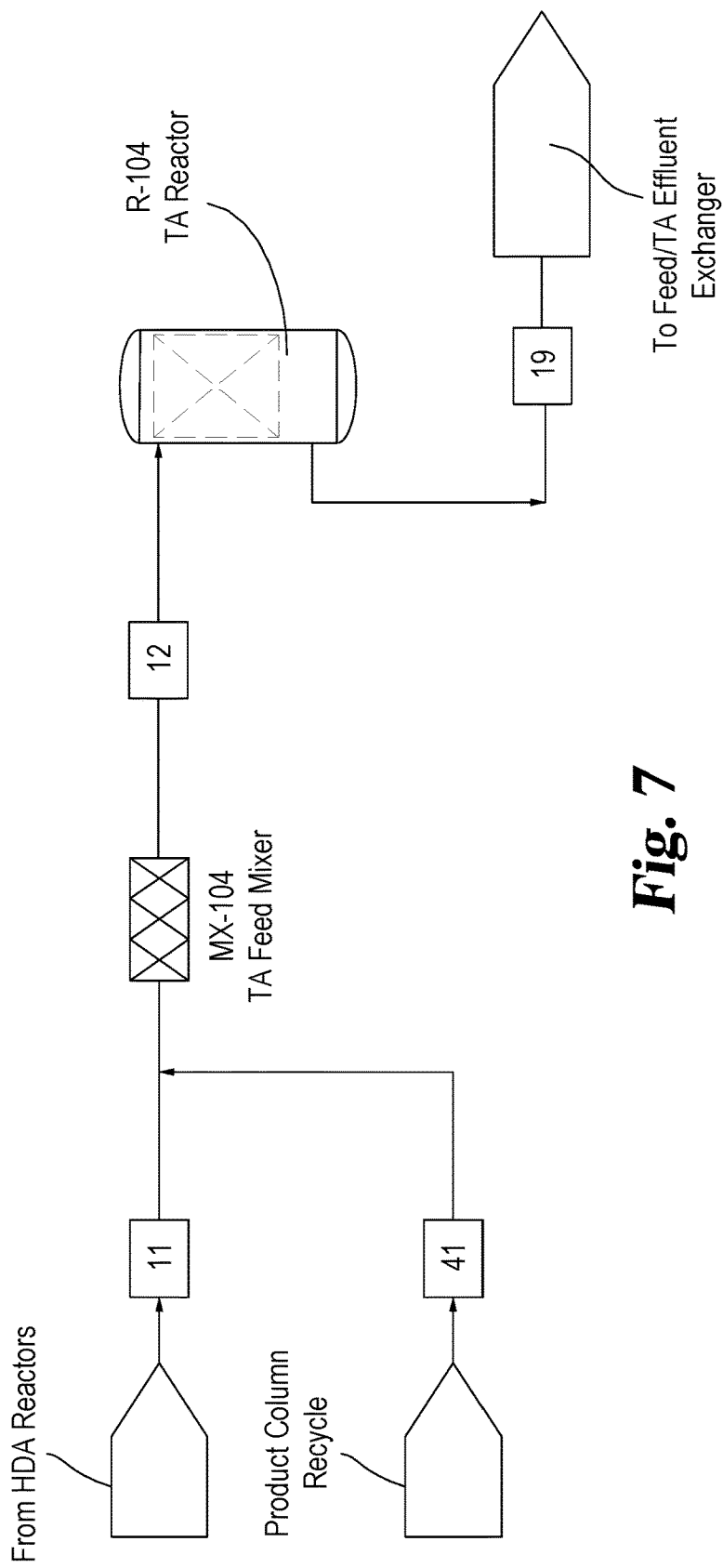
Figure 8:
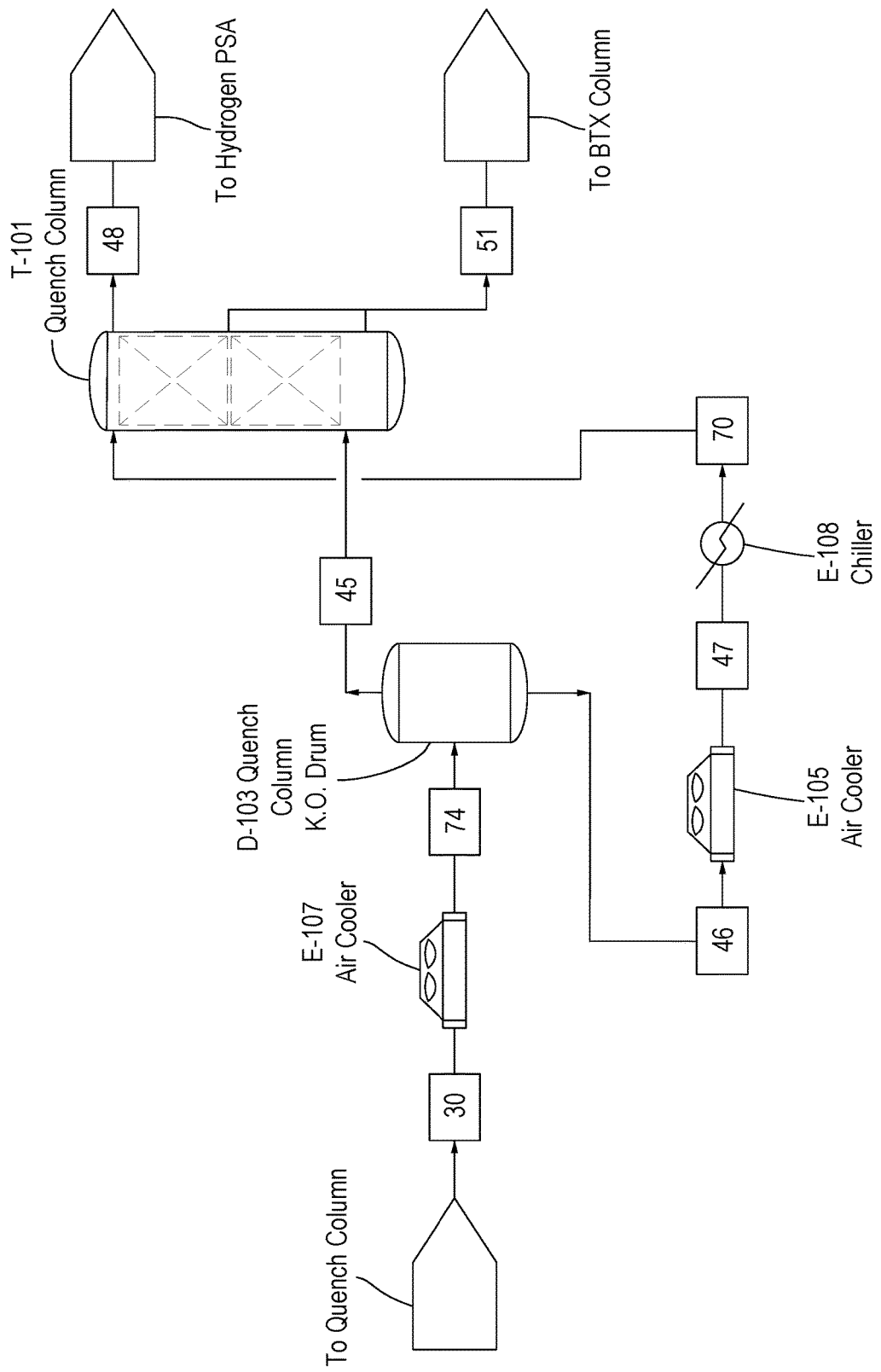
Figure 9:
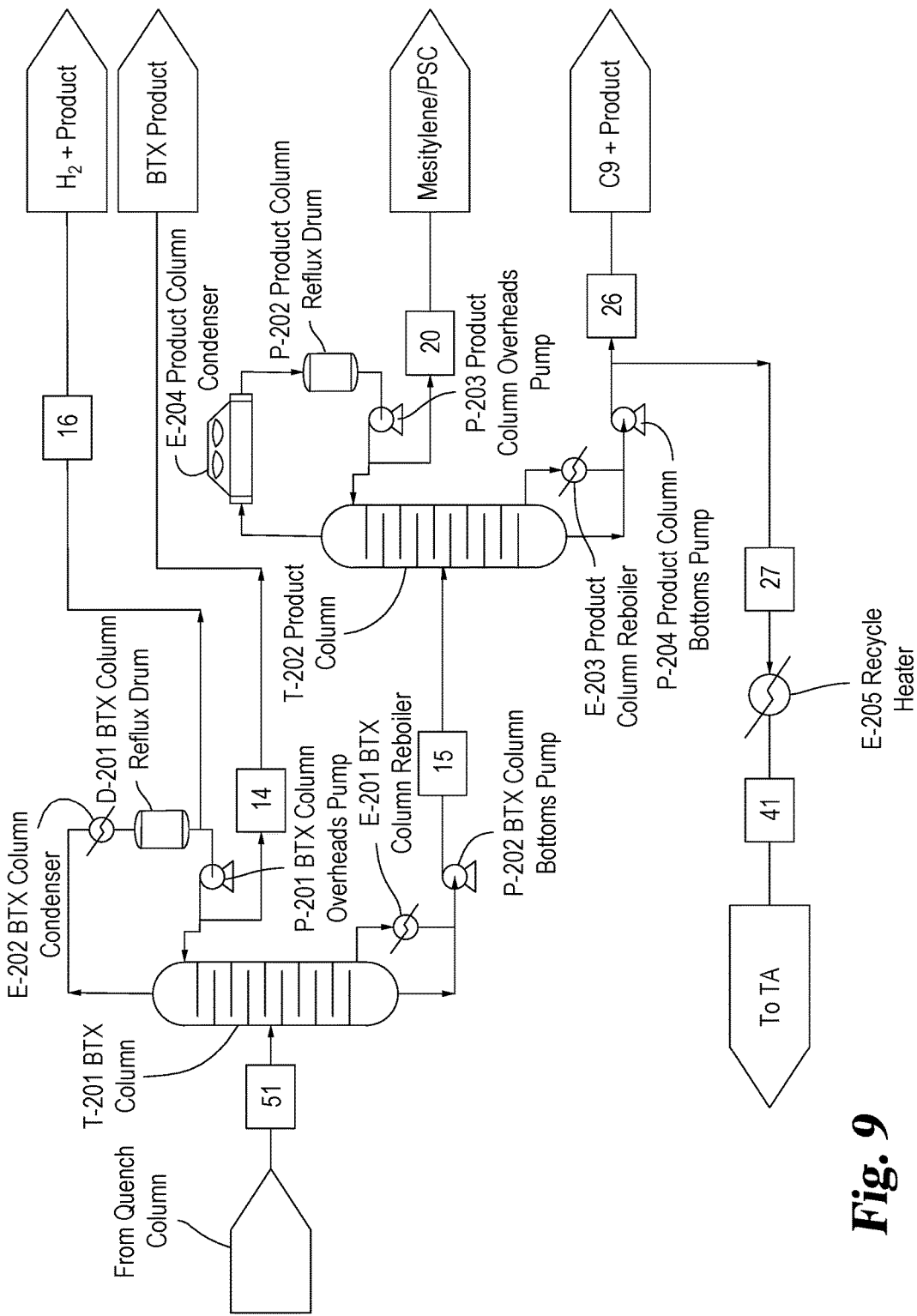
Figure 10:
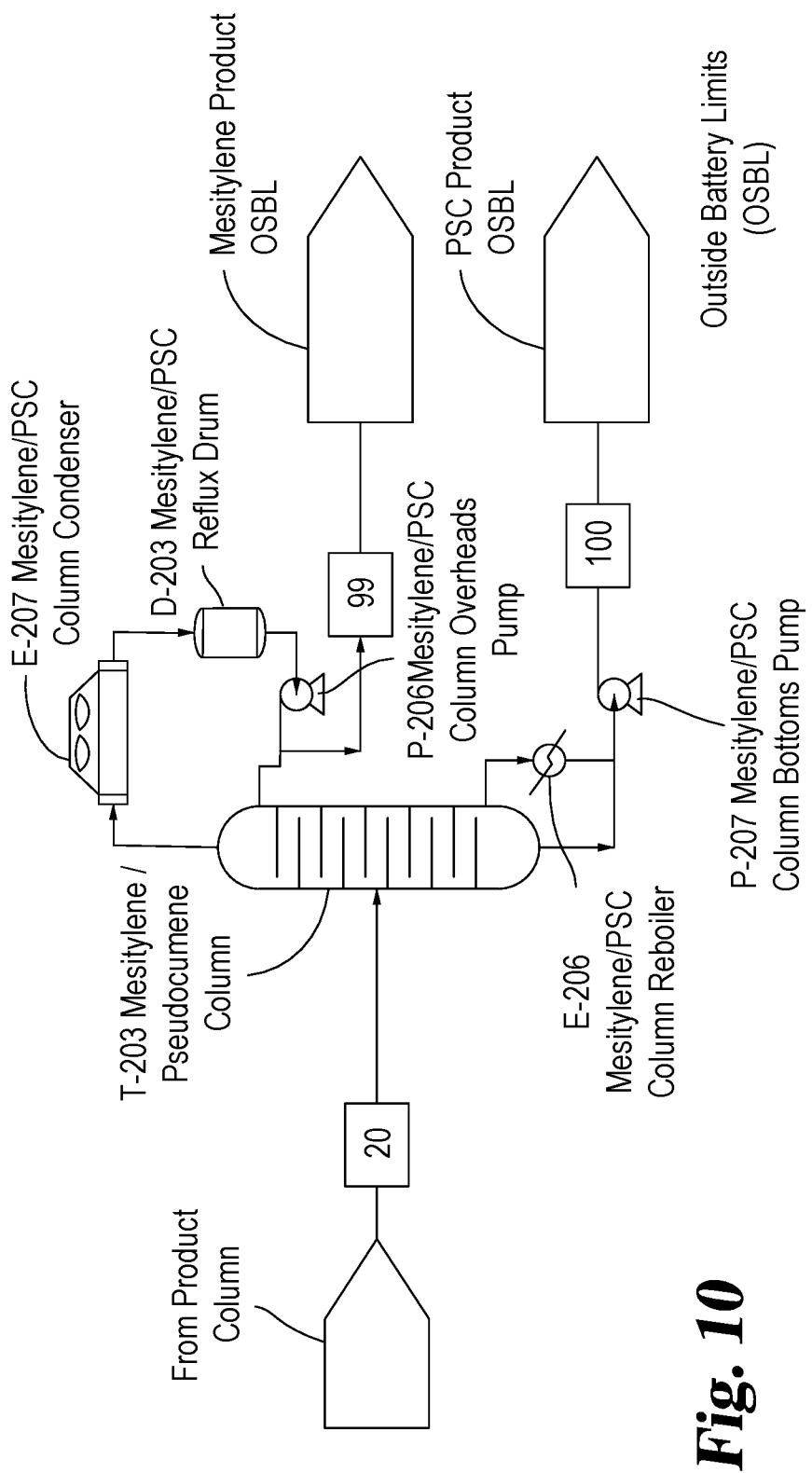
Figure 11:
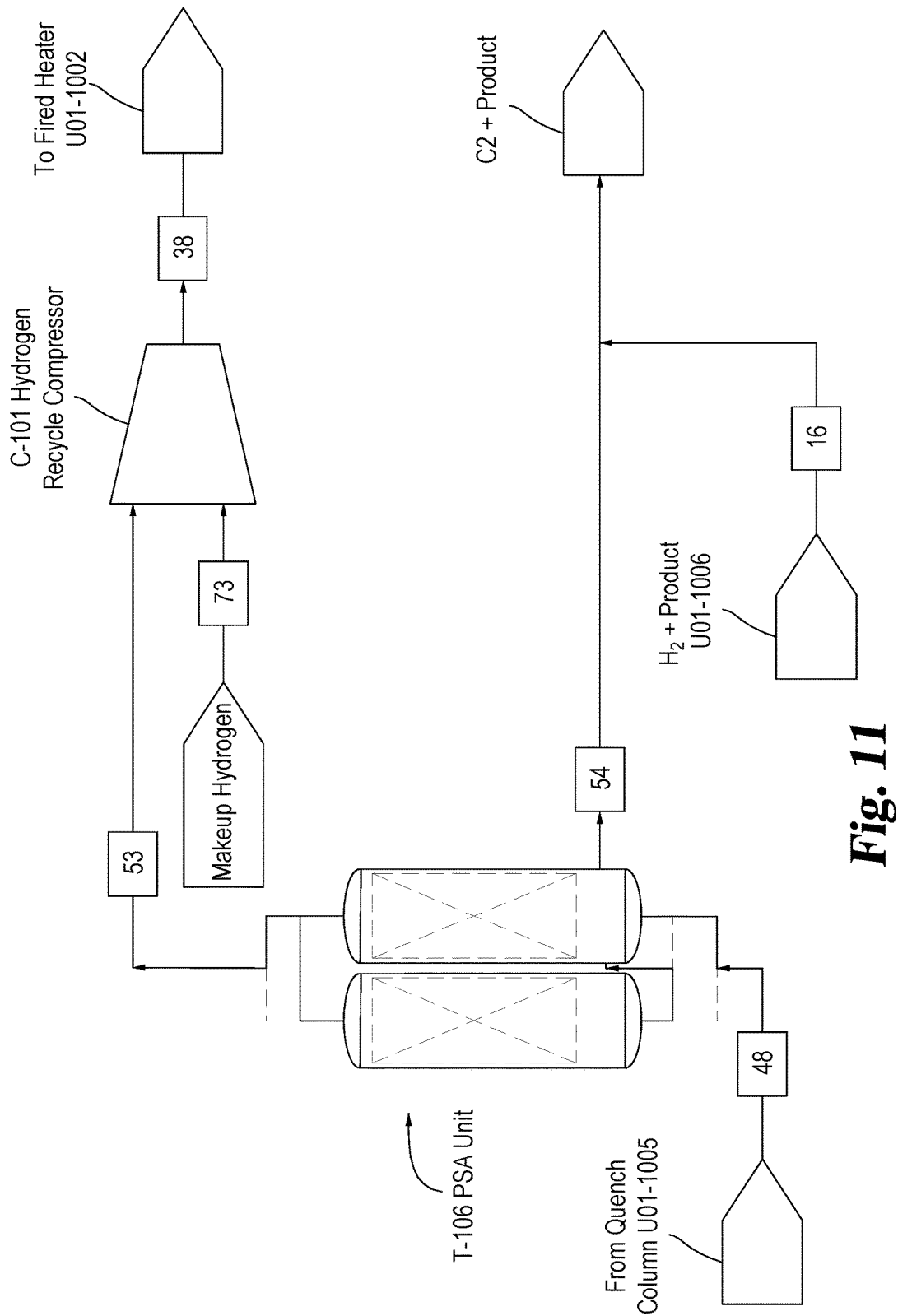
Figure 12:
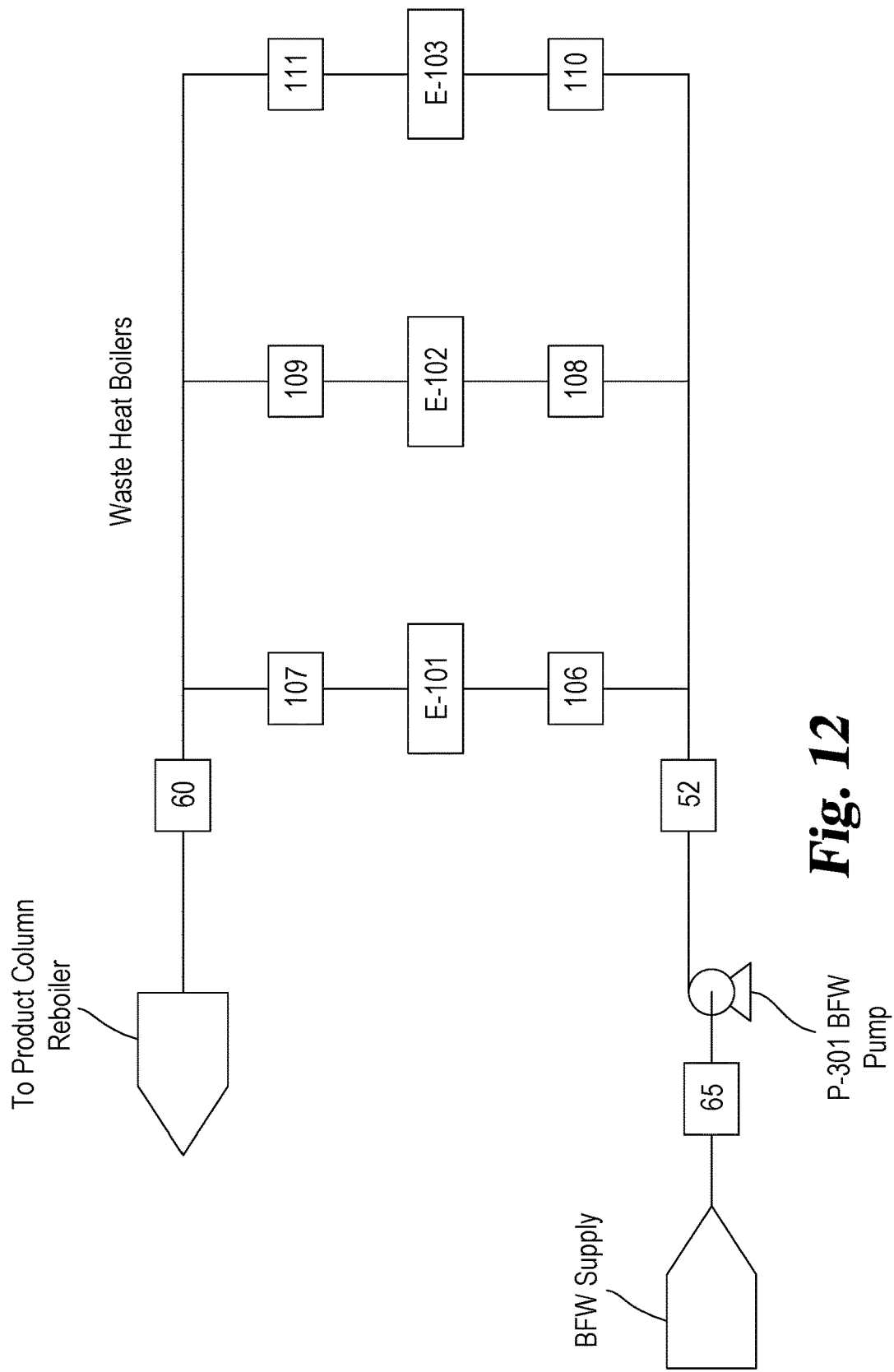
Figure 13:
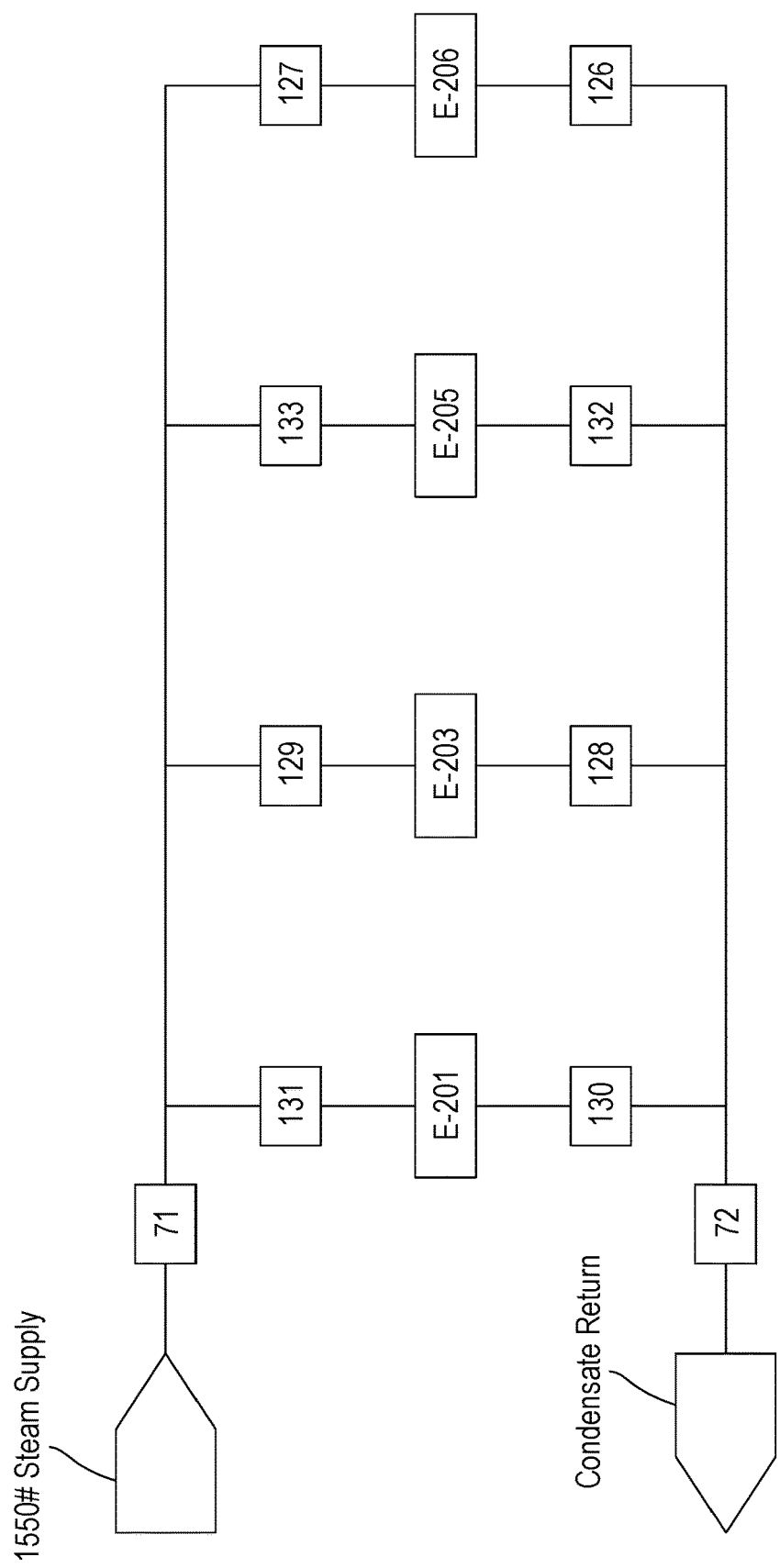
Figure 14:
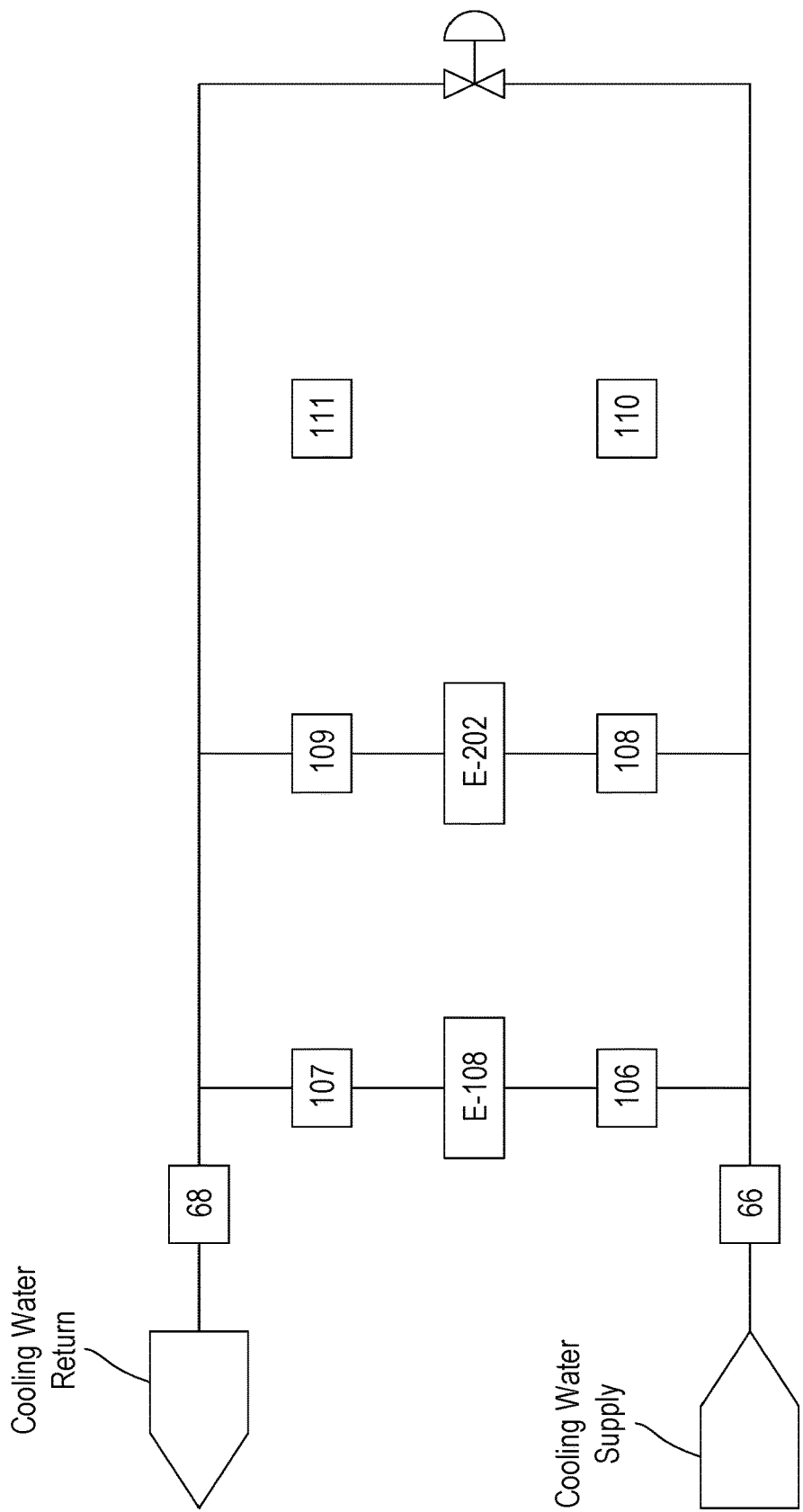
Figure 15:
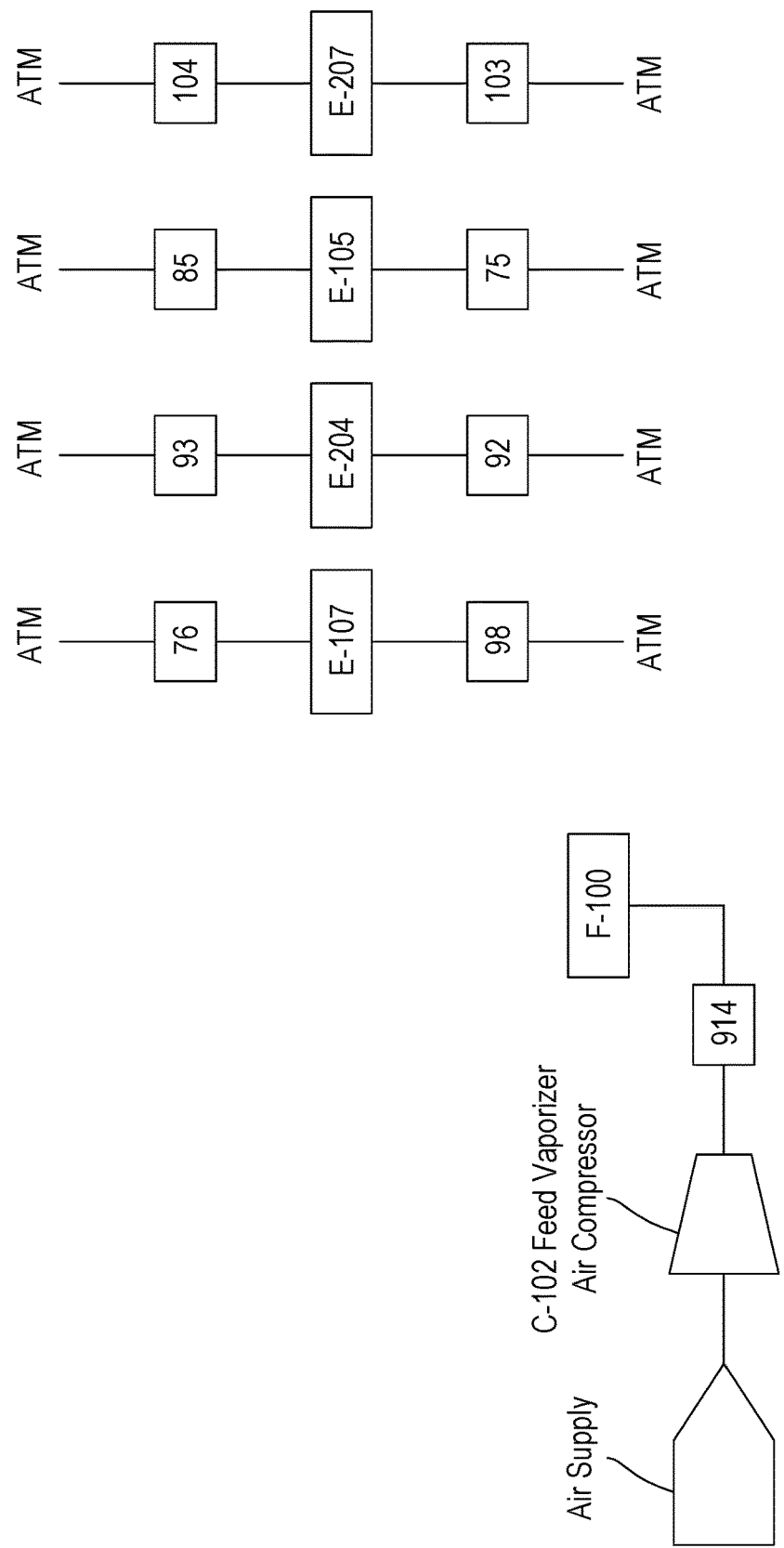
Figure 16:
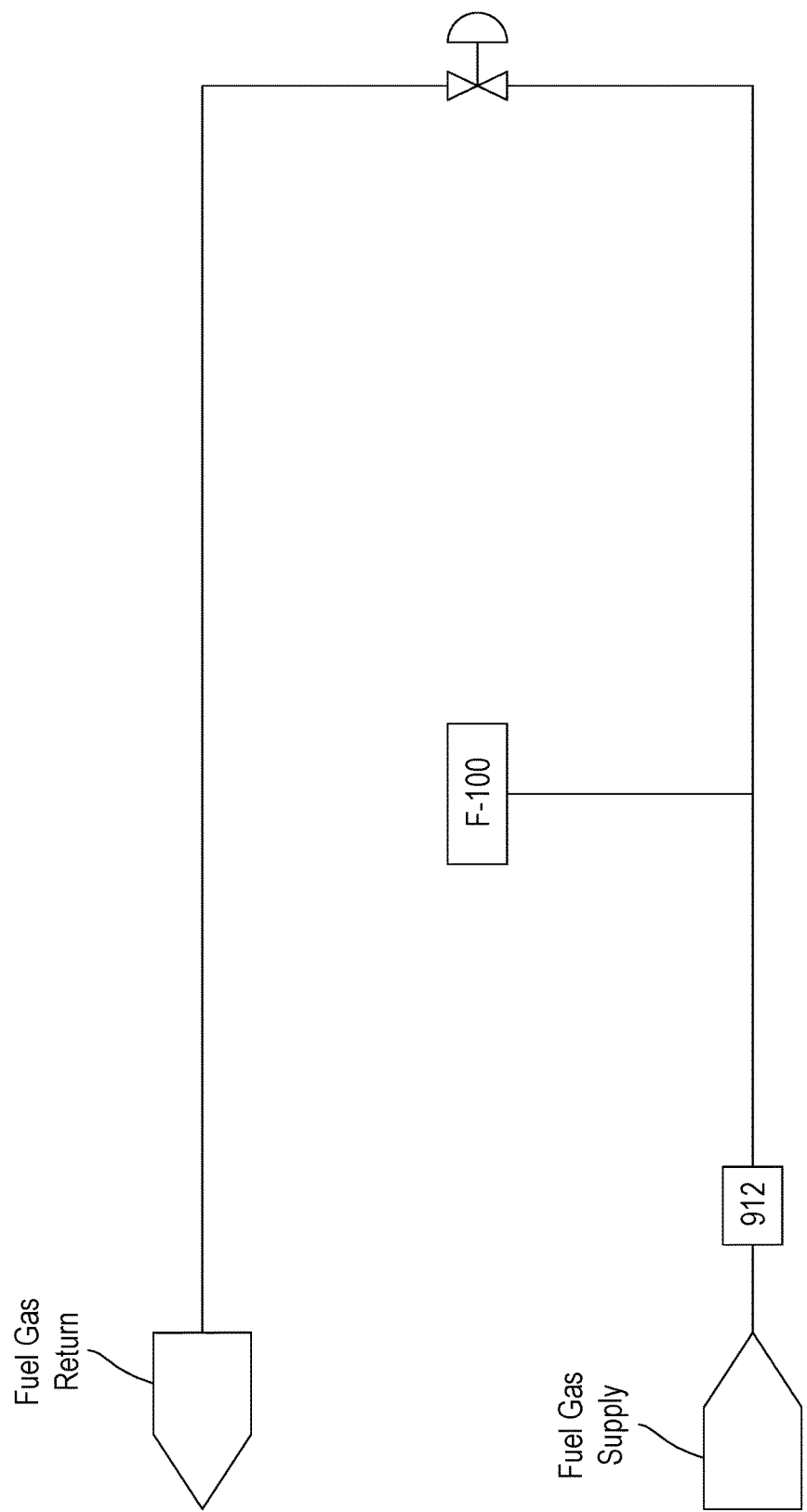

By way of further example, a heat and material balance has been prepared based on a typical C8-C10 feed stream. Referring to FIG. 4, there is shown the initial feed and preliminary processing thereof for passing the feed to the system. This composition of the feed is shown in the following table as Stream Number 1:

| | | STREAM NUMBER | |
|---|---|---|---|
| | | 1 | 2 |
| TEMPERATURE | DEG F. | 77 | 82 |
| PRESSURE | PSIA | 15 | 405 |
| COMPONENTS | | | |
| HYDROGEN | LB/HR | 0 | 0 |
| METHANE | LB/HR | 0 | 0 |
| WATER | LB/HR | 0 | 0 |
| ETHANE | LB/HR | 0 | 0 |
| PROPANE | LB/HR | 0 | 0 |
| BUTANE | LB/HR | 0 | 0 |
| TOLUENE | LB/HR | 0 | 0 |
| BENZENE | LB/HR | 0 | 0 |
| O_XYLENE | LB/HR | 0 | 0 |
| _124TRIMETHYLBENZENE | LB/HR | 23,827 | 23,827 |
| _1ETHYL2METHYLBENZENE | LB/HR | 10,808 | 10,808 |
| _1ETHYL4METHYLBENZENE | LB/HR | 5,328 | 5,328 |
| _123TRIMETHYLBENZENE | LB/HR | 4,544 | 4,544 |
| _135TRIMETHYLBENZENE | LB/HR | 3,445 | 3,445 |
| M_XYLENE | LB/HR | 1,707 | 1,707 |
| _13DIETHYLBENZENE | LB/HR | 3,392 | 3,392 |
| _2ETHYL13DIMETHYLBENZENE | LB/HR | 1,559 | 1,559 |
| _1METHYL3PROPYLBENZENE | LB/HR | 1,088 | 1,088 |
| _1ETHYL23DIMETHYLBENZENE | LB/HR | 857 | 857 |
| _1234STETRAMETHYLBENZENE | LB/HR | 1,230 | 1,230 |
| _1ETHYL24DIMETHYLBENZENE | LB/HR | 705 | 705 |
| PROPYLBENZENE | LB/HR | 571 | 571 |
| M_CYMENE | LB/HR | 486 | 486 |
| SEC_BUTYLBENZENE | LB/HR | 632 | 632 |
| _1234TETRAMETHYLBENZENE | LB/HR | 334 | 334 |
| _4ETHYL12DIMETHYLBENZENE | LB/HR | 276 | 276 |
| P_XYLENE | LB/HR | 176 | 176 |
| NAPTHALENE | LB/HR | 247 | 247 |
| BUTYLBENZENE | LB/HR | 156 | 156 |
| _12DIETHYLBENZENE | LB/HR | 113 | 113 |
| _2METHYL1PROPYLBENZENE | LB/HR | 102 | 102 |
| _123STETRAMETHYLBENZENE | LB/HR | 0 | 0 |
| PENTAMETHYLBENZENE | LB/HR | 0 | 0 |
| BICYCLOHEXYL | LB/HR | 2,496 | 2,496 |
| TOTAL | LB/HR | 64,080 | 64,080 |
| ENTHALPY | BTU/LB | −224 | −222 |
| DENSITY | LB/CUFT | 54.51 | 54.36 |
| VOLUMETRIC FLOW | GPM | 147 | 147 |

The entire system is shown diagrammatically in FIGS. 4-16. The compositions of the various streams are shown in the following tables.

| | | STREAM NUMBER | | | | | |
|---|---|---|---|---|---|---|---|
| | | 2 | 3 | 4 | 5 | 19 | 30 | 38 |
| TEMPERATURE | DEG F. | 82 | 111 | 339 | 761 | 392 | 350 | 148 |
| PRESSURE | PSIA | 405 | 405 | 405 | 400 | 330 | 330 | 405 |
| COMPONENTS | | | | | | | | |
| HYDROGEN | LB/HR | 0 | 6,281 | 6,281 | 6,281 | 5,806 | 5,806 | 6,281 |
| METHANE | LB/HR | 0 | 0 | 0 | 0 | 0 | 0 | 0 |
| WATER | LB/HR | 0 | 0 | 0 | 0 | 0 | 0 | 0 |
| ETHANE | LB/HR | 0 | 1,037 | 1,037 | 1,037 | 7,406 | 7,406 | 1,037 |

-continued

| | | | | | | | | |
|---|---|---|---|---|---|---|---|---|
| PROPANE | LB/HR | 0 | 0 | 0 | 0 | 761 | 761 | 0 |
| BUTANE | LB/HR | 0 | 0 | 0 | 0 | 341 | 341 | 0 |
| TOLUENE | LB/HR | 0 | 0 | 0 | 0 | 4,509 | 4,509 | 0 |
| BENZENE | LB/HR | 0 | 0 | 0 | 0 | 0 | 0 | 0 |
| O_XYLENE | LB/HR | 0 | 0 | 0 | 0 | 5,474 | 5,474 | 0 |
| _124TRIMETHYLBENZENE | LB/HR | 23,827 | 23,827 | 23,827 | 23,827 | 31,467 | 31,467 | 0 |
| _1ETHYL2METHYL-BENZENE | LB/HR | 10,808 | 10,808 | 10,808 | 10,808 | 0 | 0 | 0 |
| _1ETHYL4METHYL-BENZENE | LB/HR | 5,328 | 5,328 | 5,328 | 5,328 | 0 | 0 | 0 |
| _123TRIMETHYLBENZENE | LB/HR | 4,544 | 4,544 | 4,544 | 4,544 | 1,666 | 1,666 | 0 |
| _135TRIMETHYLBENZENE | LB/HR | 3,445 | 3,445 | 3,445 | 3,445 | 14,435 | 14,435 | 0 |
| M_XYLENE | LB/HR | 1,707 | 1,707 | 1,707 | 1,707 | 14,641 | 14,641 | 0 |
| _13DIETHYLBENZENE | LB/HR | 3,392 | 3,392 | 3,392 | 3,392 | 0 | 0 | 0 |
| _2ETHYL13DIMETHYL-BENZENE | LB/HR | 1,559 | 1,559 | 1,559 | 1,559 | 0 | 0 | 0 |
| _1METHYL3PROPYL-BENZENE | LB/HR | 1,088 | 1,088 | 1,088 | 1,088 | 0 | 0 | 0 |
| _1ETHYL23DIMETHYL-BENZENE | LB/HR | 857 | 857 | 857 | 857 | 0 | 0 | 0 |
| _1245TETRAMETHYL-BENZENE | LB/HR | 1,230 | 1,230 | 1,230 | 1,230 | 19,532 | 19,532 | 0 |
| _1ETHYL24DIMETHYL-BENZENE | LB/HR | 705 | 705 | 705 | 705 | 0 | 0 | 0 |
| PROPYLBENZENE | LB/HR | 571 | 571 | 571 | 571 | 0 | 0 | 0 |
| M_CYMENE | LB/HR | 486 | 486 | 486 | 486 | 0 | 0 | 0 |
| SEC_BUTYLBENZENE | LB/HR | 632 | 632 | 632 | 632 | 0 | 0 | 0 |
| _1234TETRAMETHYL-BENZENE | LB/HR | 334 | 334 | 334 | 334 | 445 | 445 | 0 |
| _4ETHYL12DIMETHYL-BENZENE | LB/HR | 276 | 276 | 276 | 276 | 0 | 0 | 0 |
| P_XYLENE | LB/HR | 176 | 176 | 176 | 176 | 5,590 | 5,590 | 0 |
| NAPTHALENE | LB/HR | 247 | 247 | 247 | 247 | 0 | 0 | 0 |
| BUTYLBENZENE | LB/HR | 156 | 156 | 156 | 156 | 0 | 0 | 0 |
| _12DIETHYLBENZENE | LB/HR | 113 | 113 | 113 | 113 | 0 | 0 | 0 |
| _2METHYL1PROPYL-BENZENE | LB/HR | 102 | 102 | 102 | 102 | 0 | 0 | 0 |
| _1235TETRAMETHYL-BENZENE | LB/HR | 0 | 0 | 0 | 0 | 5,767 | 5,767 | 0 |
| PENTAMETHYLBENZENE | LB/HR | 0 | 0 | 0 | 0 | 1,986 | 1,986 | 0 |
| BICYCLOHEXYL | LB/HR | 2,496 | 2,496 | 2,496 | 2,496 | 0 | 0 | 0 |
| TOTAL | LB/HR | 64,080 | 71,398 | 71,398 | 71,398 | 119,825 | 119,825 | 7,318 |
| ENTHALPY | BTU/LB | −222 | −195 | 5 | 431 | 56 | −63 | 42 |
| DENSITY | LB/CUFT | 54.36 | 1.46 | 1.02 | 0.59 | 1.07 | 1.33 | 0.14 |
| VOLUMETRIC_FLOW | GPM | 147 | 6,080 | 8,757 | 14,983 | 113,955 | 11,253 | 6,321 |

| | | STREAM NUMBER | | | | | | |
|---|---|---|---|---|---|---|---|---|
| | | 5 | 6 | 7 | 8 | 9 | 10 | 11 |
| TEMPERATURE | DEG F. | 761 | 932 | 751 | 932 | 761 | 932 | 392 |
| PRESSURE | PSIA | 400 | 390 | 380 | 370 | 360 | 350 | 340 |
| COMPONENTS | MW | | | | | | | |
| HYDROGEN | | 6,281 | 6,123 | 6,123 | 5,910 | 5,910 | 5,806 | 5,806 |
| METHANE | | 0 | 0 | 0 | 0 | 0 | 0 | 0 |
| WATER | | 0 | 0 | 0 | 0 | 0 | 0 | 0 |
| ETHANE | | 1,037 | 3,160 | 3,160 | 6,005 | 6,005 | 7,406 | 7,406 |
| PROPANE | | 0 | 254 | 254 | 593 | 593 | 761 | 761 |
| BUTANE | | 0 | 114 | 114 | 266 | 266 | 341 | 341 |
| TOLUENE | | 0 | 4,507 | 4,507 | 10,547 | 10,547 | 13,522 | 13,522 |
| BENZENE | | 0 | 957 | 957 | 2,239 | 2,239 | 2,870 | 2,870 |
| O_XYLENE | | 0 | 299 | 299 | 699 | 699 | 896 | 896 |
| _124TRIMETHYLBENZENE | | 23,827 | 23,827 | 23,827 | 23,827 | 23,827 | 23,827 | 23,827 |
| _1ETHYL2METHYL-BENZENE | | 10,808 | 7,205 | 7,205 | 2,378 | 2,378 | 0 | 0 |
| _1ETHYL4METHYL-BENZENE | | 5,328 | 3,552 | 3,552 | 1,172 | 1,172 | 0 | 0 |
| _123TRIMETHYLBENZENE | | 4,544 | 4,544 | 4,544 | 4,544 | 4,544 | 4,544 | 4,544 |
| _135TRIMETHYLBENZENE | | 3,445 | 3,445 | 3,445 | 3,445 | 3,445 | 3,445 | 3,445 |
| M_XYLENE | | 1,707 | 2,304 | 2,304 | 3,104 | 3,104 | 3,498 | 3,498 |
| _13DIETHYLBENZENE | | 3,392 | 2,262 | 2,262 | 746 | 746 | 0 | 0 |
| _2ETHYL13DIMETHYL-BENZENE | | 1,559 | 1,040 | 1,040 | 343 | 343 | 0 | 0 |
| _1METHYL3PROPYL-BENZENE | | 1,088 | 725 | 725 | 239 | 239 | 0 | 0 |
| _1ETHYL23DIMETHYL-BENZENE | | 857 | 572 | 572 | 189 | 189 | 0 | 0 |

-continued

| | | | | | | | | |
|---|---|---|---|---|---|---|---|---|
| _1245TETRAMETHYL-BENZENE | | 1,230 | 1,230 | 1,230 | 1,230 | 1,230 | 1,230 | 1,230 |
| _1ETHYL24DIMETHYL-BENZENE | | 705 | 470 | 470 | 155 | 155 | 0 | 0 |
| PROPYLBENZENE | | 571 | 381 | 381 | 126 | 126 | 0 | 0 |
| M_CYMENE | | 486 | 324 | 324 | 107 | 107 | 0 | 0 |
| SEC_BUTYLBENZENE | | 632 | 421 | 421 | 139 | 139 | 0 | 0 |
| _1234TETRAMETHYL-BENZENE | | 334 | 334 | 334 | 334 | 334 | 334 | 334 |
| _4ETHYL12DIMETHYL-BENZENE | | 276 | 184 | 184 | 61 | 61 | 0 | 0 |
| P_XYLENE | | 176 | 176 | 176 | 176 | 176 | 176 | 176 |
| NAPTHALENE | | 242 | 247 | 247 | 247 | 247 | 247 | 247 |
| BUTYLBENZENE | | 156 | 104 | 104 | 34 | 34 | 0 | 0 |
| _12DIETHYLBENZENE | | 113 | 75 | 75 | 25 | 25 | 0 | 0 |
| _2METHYL1PROPYL-BENZENE | | 102 | 68 | 68 | 23 | 23 | 0 | 0 |
| _1235TETRAMETHYL-BENZENE | | 0 | 0 | 0 | 0 | 0 | 0 | 0 |
| PENTAMETHYLBENZENE | | 0 | 0 | 0 | 0 | 0 | 0 | 0 |
| BICYCLOHEXYL | | 2,496 | 2,496 | 2,496 | 2,496 | 2,496 | 2,496 | 2,496 |
| TOTAL | LB/HR | 71,398 | 71,398 | 71,398 | 71,398 | 71,398 | 71,398 | 71,398 |
| ENTHALPY | BTU/LB | 431 | 560 | 412 | 534 | 386 | 520 | 65 |
| DENSITY | LB/CUFT | 0.59 | 0.51 | 0.56 | 0.48 | 0.53 | 0.46 | 0.74 |
| VOLUMETRIC_FLOW | GPM | 14,983 | 17,518 | 15,770 | 18,463 | 16,645 | 19,517 | 12,001 |

| | | STREAM NUMBER | | | |
|---|---|---|---|---|---|
| | | 11 | 12 | 19 | 41 |
| TEMPERATURE | DEG F. | 392 | 392 | 392 | 392 |
| PRESSURE | PSIA | 340 | 340 | 330 | 340 |
| COMPONENTS | MW | | | | |
| HYDROGEN | | 5,806 | 5,806 | 5,806 | 0 |
| METHANE | | 0 | 0 | 0 | 0 |
| WATER | | 0 | 0 | 0 | 0 |
| ETHANE | | 7,406 | 7,406 | 7,406 | 0 |
| PROPANE | | 761 | 761 | 761 | 0 |
| BUTANE | | 341 | 341 | 341 | 0 |
| TOLUENE | | 13,522 | 13,522 | 4,509 | 0 |
| BENZENE | | 2,870 | 2,870 | 0 | 0 |
| O_XYLENE | | 896 | 896 | 5,474 | 0 |
| _124TRIMETHYLBENZENE | | 23,827 | 45,691 | 31,467 | 21,865 |
| _1ETHYL2METHYL-BENZENE | | 0 | 0 | 0 | 0 |
| _1ETHYL4METHYL-BENZENE | | 0 | 0 | 0 | 0 |
| _123TRIMETHYLBENZENE | | 4,544 | 6,040 | 1,666 | 1,497 |
| _135TRIMETHYLBENZENE | | 3,445 | 3,561 | 14,435 | 115 |
| M_XYLENE | | 3,498 | 3,498 | 14,641 | 0 |
| _13DIETHYLBENZENE | | 0 | 0 | 0 | 0 |
| _2ETHYL13DIMETHYL-BENZENE | | 0 | 0 | 0 | 0 |
| _1METHYL3PROPYL-BENZENE | | 0 | 0 | 0 | 0 |
| _1ETHYL23DIMETHYL-BENZENE | | 0 | 0 | 0 | 0 |
| _1245TETRAMETHYL-BENZENE | | 1,230 | 18,803 | 19,532 | 17,573 |
| _1ETHYL24DIMETHYL-BENZENE | | 0 | 0 | 0 | 0 |
| PROPYLBENZENE | | 0 | 0 | 0 | 0 |
| M_CYMENE | | 0 | 0 | 0 | 0 |
| SEC_BUTYLBENZENE | | 0 | 0 | 0 | 0 |
| _1234TETRAMETHYL-BENZENE | | 334 | 734 | 445 | 400 |
| _4ETHYL12DIMETHYL-BENZENE | | 0 | 0 | 0 | 0 |
| P_XYLENE | | 176 | 176 | 5,590 | 0 |
| NAPTHALENE | | 247 | 247 | 0 | 0 |
| BUTYLBENZENE | | 0 | 0 | 0 | 0 |
| _12DIETHYLBENZENE | | 0 | 0 | 0 | 0 |
| _2METHYL1PROPYL-BENZENE | | 0 | 0 | 0 | 0 |
| _1235TETRAMETHYL-BENZENE | | 0 | 5,189 | 5,767 | 5,189 |

-continued

| | | | | | |
|---|---|---|---|---|---|
| PENTAMETHYLBENZENE | | 0 | 1,787 | 1,986 | 1,787 |
| BICYCLOHEXYL | | 2,496 | 2,496 | 0 | 0 |
| TOTAL | LB/HR | 71,398 | 119,825 | 119,825 | 48,427 |
| ENTHALPY | BTU/LB | 63 | −6 | 56 | −111 |
| DENSITY | LB/CUFT | 0.74 | 1.24 | 1.07 | 45.27 |
| VOLUMETRIC_FLOW | GPM | 12,001 | 12,063 | 13,955 | 133 |

| | | STREAM NUMBER | | | | | | | |
|---|---|---|---|---|---|---|---|---|---|
| | | 30 | 45 | 46 | 47 | 48 | 51 | 70 | 74 |
| TEMPERATURE | DEG F. | 350 | 200 | 200 | 150 | 101 | 159 | 100 | 200 |
| PRESSURE | PSIA | 330 | 335 | 335 | 330 | 320 | 321 | 330 | 340 |
| COMPONENTS | MW | | | | | | | | |
| HYDROGEN | | 5,806 | 5,803 | 3 | 3 | 3,803 | 3 | 3 | 5,806 |
| METHANE | | 0 | 0 | 0 | 0 | 0 | 0 | 0 | 0 |
| WATER | | 0 | 0 | 0 | 0 | 0 | 0 | 0 | 0 |
| ETHANE | | 7,406 | 7,067 | 339 | 339 | 6,914 | 492 | 339 | 7,406 |
| PROPANE | | 761 | 654 | 107 | 107 | 574 | 187 | 107 | 761 |
| BUTANE | | 341 | 230 | 112 | 112 | 71 | 270 | 112 | 341 |
| TOLUENE | | 4,509 | 389 | 4,120 | 4,120 | 48 | 4,461 | 4,120 | 4,509 |
| BENZENE | | 0 | 0 | 0 | 0 | 0 | 0 | 0 | 0 |
| O_XYLENE | | 5,474 | 168 | 5,306 | 5,306 | 15 | 5,459 | 5,306 | 5,474 |
| _124TRIMETHYLBENZENE | | 31,467 | 425 | 31,042 | 31,042 | 31 | 31,436 | 31,042 | 31,467 |
| _1ETHYL2METHYL-BENZENE | | 0 | 0 | 0 | 0 | 0 | 0 | 0 | 0 |
| _1ETHYL4METHYL-BENZENE | | 0 | 0 | 0 | 0 | 0 | 0 | 0 | 0 |
| _123TRIMETHYLBENZENE | | 1,666 | 18 | 1,648 | 1,648 | 1 | 1,664 | 1,648 | 1,666 |
| _135TRIMETHYLBENZENE | | 14,435 | 217 | 14,218 | 14,218 | 16 | 14,420 | 14,218 | 14,435 |
| M_XYLENE | | 14,641 | 539 | 14,102 | 14,102 | 52 | 14,589 | 14,102 | 14,641 |
| _13DIETHYLBENZENE | | 0 | 0 | 0 | 0 | 0 | 0 | 0 | 0 |
| _2ETHYL13DIMETHYL-BENZENE | | 0 | 0 | 0 | 0 | 0 | 0 | 0 | 0 |
| _1METHYL3PROPYL-BENZENE | | 0 | 0 | 0 | 0 | 0 | 0 | 0 | 0 |
| _1ETHYL23DIMETHYL-BENZENE | | 0 | 0 | 0 | 0 | 0 | 0 | 0 | 0 |
| _1245TETRAMETHYL-BENZENE | | 19,532 | 102 | 19,430 | 19,430 | 0 | 19,526 | 19,430 | 19,532 |
| _1ETHYL24DIMETHYL-BENZENE | | 0 | 0 | 0 | 0 | 0 | 0 | 0 | 0 |
| PROPYLBENZENE | | 0 | 0 | 0 | 0 | 0 | 0 | 0 | 0 |
| M_CYMENE | | 0 | 0 | 0 | 0 | 0 | 0 | 0 | 0 |
| SEC_BUTYLBENZENE | | 0 | 0 | 0 | 0 | 0 | 0 | 0 | 0 |
| _1234TETRAMETHYL-BENZENE | | 445 | 2 | 443 | 443 | 0 | 445 | 443 | 445 |
| _4ETHYL12DIMETHYL-BENZENE | | 0 | 0 | 0 | 0 | 0 | 0 | 0 | 0 |
| P_XYLENE | | 5,590 | 210 | 5,380 | 5,380 | 20 | 5,569 | 5,380 | 5,590 |
| NAPTHALENE | | 0 | 0 | 0 | 0 | 0 | 0 | 0 | 0 |
| BUTYLBENZENE | | 0 | 0 | 0 | 0 | 0 | 0 | 0 | 0 |
| _12DIETHYLBENZENE | | 0 | 0 | 0 | 0 | 0 | 0 | 0 | 0 |
| _2METHYL1PROPYL-BENZENE | | 0 | 0 | 0 | 0 | 0 | 0 | 0 | 0 |
| _1235TETRAMETHYL-BENZENE | | 5,767 | 28 | 5,738 | 5,738 | 1 | 5,765 | 5,738 | 5,767 |
| PENTAMETHYLBENZENE | | 1,986 | 3 | 1,983 | 1,983 | 0 | 1,986 | 1,983 | 1,986 |
| BICYCLOHEXYL | | 0 | 0 | 0 | 0 | 0 | 0 | 0 | 0 |
| TOTAL | LB/HR | 119,825 | 15,856 | 103,969 | 103,969 | 13,553 | 106,272 | 103,969 | 119,825 |
| ENTHALPY | BTU/LB | −63 | −396 | −158 | −182 | −618 | −179 | −203 | −190 |
| DENSITY | LB/CUFT | 1.33 | 0.24 | 50.49 | 52.01 | 0.23 | 51.57 | 53.47 | 1.77 |
| VOLUMETRIC_FLOW | GPM | 11,253 | 8,303 | 257 | 249 | 7,326 | 257 | 242 | 8,438 |

| | | STREAM NUMBER | | | | | | | |
|---|---|---|---|---|---|---|---|---|---|
| | | 14 | 15 | 16 | 20 | 26 | 27 | 41 | 51 |
| TEMPERATURE | DEG F. | 95 | 376 | 95 | 331 | 401 | 401 | 392 | 159 |
| PRESSURE | PSIA | 15 | 21 | 15 | 15 | 340 | 340 | 340 | 321 |
| COMPONENTS | MW | | | | | | | | |
| HYDROGEN | | 0 | 0 | 3 | 0 | 0 | 0 | 0 | 3 |
| METHANE | | 0 | 0 | 0 | 0 | 0 | 0 | 0 | 0 |
| WATER | | 0 | 0 | 0 | 0 | 0 | 0 | 0 | 0 |
| ETHANE | | 137 | 0 | 355 | 0 | 0 | 0 | 0 | 492 |
| PROPANE | | 116 | 0 | 71 | 0 | 0 | 0 | 0 | 187 |
| BUTANE | | 232 | 0 | 38 | 0 | 0 | 0 | 0 | 270 |

-continued

| | | | | | | | | | |
|---|---|---|---|---|---|---|---|---|---|
| TOLUENE | | 4,446 | 0 | 15 | 0 | 0 | 0 | 0 | 4,461 |
| BENZENE | | 0 | 0 | 0 | 0 | 0 | 0 | 0 | 0 |
| O_XYLENE | | 5,364 | 92 | 4 | 92 | 0 | 0 | 0 | 5,459 |
| _124TRIMETHYLBENZENE | | 0 | 31,436 | 0 | 7,142 | 2,429 | 21,865 | 21,865 | 31,436 |
| _1ETHYL2METHYL-BENZENE | | 0 | 0 | 0 | 0 | 0 | 0 | 0 | 0 |
| _1ETHYL4METHYL-BENZENE | | 0 | 0 | 0 | 0 | 0 | 0 | 0 | 0 |
| _123TRIMETHYLBENZENE | | 0 | 1,664 | 0 | 2 | 166 | 1,497 | 1,497 | 1,664 |
| _135TRIMETHYLBENZENE | | 0 | 14,420 | 0 | 14,291 | 13 | 115 | 115 | 14,420 |
| M_XYLENE | | 14,573 | 1 | 15 | 1 | 0 | 0 | 0 | 14,589 |
| _13DIETHYLBENZENE | | 0 | 0 | 0 | 0 | 0 | 0 | 0 | 0 |
| _2ETHYL13DIMETHYL-BENZENE | | 0 | 0 | 0 | 0 | 0 | 0 | 0 | 0 |
| _1METHYL3PROPYL-BENZENE | | 0 | 0 | 0 | 0 | 0 | 0 | 0 | 0 |
| _1ETHYL23DIMETHYL-BENZENE | | 0 | 0 | 0 | 0 | 0 | 0 | 0 | 0 |
| _1245TETRAMETHYL-BENZENE | | 0 | 19,526 | 0 | 0 | 1,953 | 17,573 | 17,573 | 19,526 |
| _1ETHYL24DIMETHYL-BENZENE | | 0 | 0 | 0 | 0 | 0 | 0 | 0 | 0 |
| PROPYLBENZENE | | 0 | 0 | 0 | 0 | 0 | 0 | 0 | 0 |
| M_CYMENE | | 0 | 0 | 0 | 0 | 0 | 0 | 0 | 0 |
| SEC_BUTYLBENZENE | | 0 | 0 | 0 | 0 | 0 | 0 | 0 | 0 |
| _1234TETRAMETHYL-BENZENE | | 0 | 445 | 0 | 0 | 44 | 400 | 400 | 445 |
| _4ETHYL12DIMETHYL-BENZENE | | 0 | 0 | 0 | 0 | 0 | 0 | 0 | 0 |
| P_XYLENE | | 5,563 | 0 | 0 | 0 | 0 | 0 | 0 | 5,569 |
| NAPTHALENE | | 0 | 0 | 0 | 0 | 0 | 0 | 0 | 0 |
| BUTYLBENZENE | | 0 | 0 | 0 | 0 | 0 | 0 | 0 | 0 |
| _12DIETHYLBENZENE | | 0 | 0 | 0 | 0 | 0 | 0 | 0 | 0 |
| _2METHYL1PROPYL-BENZENE | | 0 | 0 | 0 | 0 | 0 | 0 | 0 | 0 |
| _1235TETRAMETHYL-BENZENE | | 0 | 5,765 | 0 | 0 | 577 | 5,189 | 5,189 | 5,765 |
| PENTAMETHYLBENZENE | | 0 | 1,986 | 0 | 0 | 199 | 1,787 | 1,787 | 1,986 |
| BICYCLOHEXYL | | 0 | 0 | 0 | 0 | 0 | 0 | 0 | 0 |
| TOTAL | LB/HR | 30,430 | 75,335 | 507 | 21,528 | 5,381 | 48,427 | 48,427 | 106,272 |
| ENTHALPY | BTU/LB | −88 | −108 | −1,034 | −103 | −105 | −105 | −111 | −179 |
| DENSITY | LB/CUFT | 52.91 | 45.44 | 0.08 | 46.07 | 44.93 | 44.93 | 45.27 | 51.57 |
| VOLUMETRIC_FLOW | GPM | 72 | 207 | 795 | 58 | 15 | 134 | 133 | 257 |

| | | STREAM NUMBER | | |
|---|---|---|---|---|
| | | 20 | 99 | 100 |
| TEMPERATURE | DEG F. | 331 | 328 | 380 |
| PRESSURE | PSIA | 15 | 15 | 26 |
| COMPONENTS | MW | | | |
| HYDROGEN | | 0 | 0 | 0 |
| METHANE | | 0 | 0 | 0 |
| WATER | | 0 | 0 | 0 |
| ETHANE | | 0 | 0 | 0 |
| PROPANE | | 0 | 0 | 0 |
| BUTANE | | 0 | 0 | 0 |
| TOLUENE | | 0 | 0 | 0 |
| BENZENE | | 0 | 0 | 0 |
| O_XYLENE | | 92 | 92 | 0 |
| _124TRIMETHYLBENZENE | | 7,142 | 474 | 6,668 |
| _1ETHYL2METHYL-BENZENE | | 0 | 0 | 0 |
| _1ETHYL4METHYL-BENZENE | | 0 | 0 | 0 |
| _123TRIMETHYLBENZENE | | 2 | 0 | 2 |
| _135TRIMETHYLBENZENE | | 14,291 | 14,068 | 223 |
| M_XYLENE | | 1 | 1 | 0 |
| _13DIETHYLBENZENE | | 0 | 0 | 0 |
| _2ETHYL13DIMETHYL-BENZENE | | 0 | 0 | 0 |
| _1METHYL3PROPYL-BENZENE | | 0 | 0 | 0 |
| _1ETHYL23DIMETHYL-BENZENE | | 0 | 0 | 0 |
| _1245TETRAMETHYL-BENZENE | | 0 | 0 | 0 |

-continued

| | | | | |
|---|---|---|---|---|
| _1ETHYL24DIMETHYL-BENZENE | | 0 | 0 | 0 |
| PROPYLBENZENE | | 0 | 0 | 0 |
| M_CYMENE | | 0 | 0 | 0 |
| SEC_BUTYLBENZENE | | 0 | 0 | 0 |
| _1234TETRAMETHYL-BENZENE | | 0 | 0 | 0 |
| _4ETHYL12DIMETHYL-BENZENE | | 0 | 0 | 0 |
| P_XYLENE | | 0 | 0 | 0 |
| NAPTHALENE | | 0 | 0 | 0 |
| BUTYLBENZENE | | 0 | 0 | 0 |
| _12DIETHYLBENZENE | | 0 | 0 | 0 |
| _2METHYL1PROPYL-BENZENE | | 0 | 0 | 0 |
| _1235TETRAMETHYL-BENZENE | | 0 | 0 | 0 |
| PENTAMETHYLBENZENE | | 0 | 0 | 0 |
| BICYCLOHEXYL | | 0 | 0 | 0 |
| TOTAL | LB/HR | 21,528 | 14,635 | 6,893 |
| ENTHALPY | BTU/LB | −103 | −106 | −69 |
| DENSITY | LB/CUFT | 46.07 | 45.90 | 44.86 |
| VOLUMETRIC_FLOW | GPM | 58 | 40 | 19 |

| | | STREAM NUMBER | | | | | |
|---|---|---|---|---|---|---|---|
| | | 16 | 38 | 48 | 53 | 54 | 73 |
| TEMPERATURE | DEG F. | 95 | 148 | 101 | 101 | 101 | 77 |
| PRESSURE | PSIA | 15 | 405 | 320 | 320 | 320 | 405 |
| COMPONENTS | MW | | | | | | |
| HYDROGEN | | 3 | 6,281 | 5,803 | 5,803 | 0 | 478 |
| METHANE | | 0 | 0 | 0 | 0 | 0 | 0 |
| WATER | | 0 | 0 | 0 | 0 | 0 | 0 |
| ETHANE | | 355 | 1,037 | 6,914 | 1,037 | 5,877 | 0 |
| PROPANE | | 71 | 0 | 574 | 0 | 574 | 0 |
| BUTANE | | 38 | 0 | 71 | 0 | 71 | 0 |
| TOLUENE | | 15 | 0 | 48 | 0 | 48 | 0 |
| BENZENE | | 0 | 0 | 0 | 0 | 0 | 0 |
| O_XYLENE | | 4 | 0 | 15 | 0 | 15 | 0 |
| _124TRIMETHYLBENZENE | | 0 | 0 | 31 | 0 | 31 | 0 |
| _1ETHYL2METHYL-BENZENE | | 0 | 0 | 0 | 0 | 0 | 0 |
| _1ETHYL4METHYL-BENZENE | | 0 | 0 | 0 | 0 | 0 | 0 |
| _123TRIMETHYLBENZENE | | 0 | 0 | 1 | 0 | 1 | 0 |
| _135TRIMETHYLBENZENE | | 0 | 0 | 16 | 0 | 16 | 0 |
| M_XYLENE | | 15 | 0 | 52 | 0 | 52 | 0 |
| _13DIETHYLBENZENE | | 0 | 0 | 0 | 0 | 0 | 0 |
| _2ETHYL13DIMETHYL-BENZENE | | 0 | 0 | 0 | 0 | 0 | 0 |
| _1METHYL3PROPYL-BENZENE | | 0 | 0 | 0 | 0 | 0 | 0 |
| _1ETHYL23DIMETHYL-BENZENE | | 0 | 0 | 0 | 0 | 0 | 0 |
| _1245TETRAMETHYL-BENZENE | | 0 | 0 | 6 | 0 | 0 | 0 |
| _1ETHYL24DIMETHYL-BENZENE | | 0 | 0 | 0 | 0 | 0 | 0 |
| PROPYLBENZENE | | 0 | 0 | 0 | 0 | 0 | 0 |
| M_CYMENE | | 0 | 0 | 0 | 0 | 0 | 0 |
| SEC_BUTYLBENZENE | | 0 | 0 | 0 | 0 | 0 | 0 |
| _1234TETRAMETHYL-BENZENE | | 0 | 0 | 0 | 0 | 0 | 0 |
| _4ETHYL12DIMETHYL-BENZENE | | 0 | 0 | 0 | 0 | 0 | 0 |
| P_XYLENE | | 6 | 0 | 20 | 0 | 20 | 0 |
| NAPTHALENE | | 0 | 0 | 0 | 0 | 0 | 0 |
| BUTYLBENZENE | | 0 | 0 | 0 | 0 | 0 | 0 |
| _12DIETHYLBENZENE | | 0 | 0 | 0 | 0 | 0 | 0 |
| _2METHYL1PROPYL-BENZENE | | 0 | 0 | 0 | 0 | 0 | 0 |
| _1235TETRAMETHYL-BENZENE | | 0 | 0 | 1 | 0 | 1 | 0 |

-continued

|  |  |  |  |  |  |  |  |
|---|---|---|---|---|---|---|---|
| PENTAMETHYLBENZENE |  | 0 | 0 | 0 | 0 | 0 | 0 |
| BICYCLOHEXYL |  | 0 | 0 | 0 | 0 | 0 | 0 |
| TOTAL | LB/HR | 507 | 7,318 | 13,553 | 6,840 | 6,712 | 478 |
| ENTHALPY | BTU/LB | −1,034 | 42 | −618 | −110 | −1,139 | 0 |
| DENSITY | LB/CUFT | 0.08 | 0.14 | 0.23 | 0.12 | 1.71 | 0.14 |
| VOLUMETRIC_FLOW | GPM | 795 | 6,321 | 7,326 | 6,830 | 489 | 420 |

| | | STREAM NUMBER | | | | | | | | |
|---|---|---|---|---|---|---|---|---|---|---|
| | | 52 | 60 | 65 | 106 | 107 | 108 | 109 | 110 | 111 |
| TEMPERATURE | DEG F. | 212 | 466 | 210 | 212 | 466 | 212 | 466 | 212 | 466 |
| PRESSURE | PSIA | 500 | 495 | 15 | 500 | 495 | 500 | 495 | 500 | 495 |
| COMPONENTS | | | | | | | | | | |
| HYDROGEN | LB/HR | 0 | 0 | 0 | 0 | 0 | 0 | 0 | 0 | 0 |
| METHANE | LB/HR | 0 | 0 | 0 | 0 | 0 | 0 | 0 | 0 | 0 |
| WATER | LB/HR | 49,194 | 49,194 | 49,194 | 9,723 | 9,723 | 9,664 | 9,664 | 29,807 | 29,807 |
| ETHANE | LB/HR | 0 | 0 | 0 | 0 | 0 | 0 | 0 | 0 | 0 |
| PROPANE | LB/HR | 0 | 0 | 0 | 0 | 0 | 0 | 0 | 0 | 0 |
| BUTANE | LB/HR | 0 | 0 | 0 | 0 | 0 | 0 | 0 | 0 | 0 |
| TOLUENE | LB/HR | 0 | 0 | 0 | 0 | 0 | 0 | 0 | 0 | 0 |
| BENZENE | LB/HR | 0 | 0 | 0 | 0 | 0 | 0 | 0 | 0 | 0 |
| OXYGEN | LB/HR | 0 | 0 | 0 | 0 | 0 | 0 | 0 | 0 | 0 |
| CARBON_DIOXIDE | LB/HR | 0 | 0 | 0 | 0 | 0 | 0 | 0 | 0 | 0 |
| NITROGEN | LB/HR | 0 | 0 | 0 | 0 | 0 | 0 | 0 | 0 | 0 |
| PENTENE | LB/HR | 0 | 0 | 0 | 0 | 0 | 0 | 0 | 0 | 0 |
| DICYCLO-PENTADIENE | LB/HR | 0 | 0 | 0 | 0 | 0 | 0 | 0 | 0 | 0 |
| HEPTENE | LB/HR | 0 | 0 | 0 | 0 | 0 | 0 | 0 | 0 | 0 |
| OCTANE | LB/HR | 0 | 0 | 0 | 0 | 0 | 0 | 0 | 0 | 0 |
| OCTENE | LB/HR | 0 | 0 | 0 | 0 | 0 | 0 | 0 | 0 | 0 |
| NONANE | LB/HR | 0 | 0 | 0 | 0 | 0 | 0 | 0 | 0 | 0 |
| DECANE | LB/HR | 0 | 0 | 0 | 0 | 0 | 0 | 0 | 0 | 0 |
| STYRENE | LB/HR | 0 | 0 | 0 | 0 | 0 | 0 | 0 | 0 | 0 |
| TOTAL | LB/HR | 49,194 | 49,194 | 49,194 | 9,723 | 9,723 | 9,664 | 9,664 | 29,807 | 29,807 |
| ENTHALPY | BTU/LB | −6,683 | −5,593 | −6,686 | −6,683 | −5,593 | −6,683 | −5,593 | −6,683 | 5,593 |
| DENSITY | LB/CUFT | 57.31 | 0.09 | 57.40 | 57.31 | 0.90 | 57.31 | 0.90 | 57.31 | 0.90 |
| VOLUMETRIC FLOW | GPM | 107 | 6,833 | 107 | 21 | 1,351 | 21 | 1,342 | 65 | 4,140 |

| | | STREAM NUMBER | | | | | | | | | |
|---|---|---|---|---|---|---|---|---|---|---|---|
| | | 71 | 72 | 126 | 127 | 128 | 129 | 130 | 131 | 132 | 133 |
| TEMPERATURE | DEG F. | 466 | 466 | 466 | 466 | 466 | 466 | 466 | 466 | #N/A | #N/A |
| PRESSURE | PSIA | 495 | 495 | 495 | 495 | 495 | 495 | 495 | 495 | #N/A | #N/A |
| COMPONENTS | | | | | | | | | | | |
| HYDROGEN | LB/HR | 0 | 0 | 0 | 0 | 0 | 0 | 0 | 0 | #N/A | #N/A |
| METHANE | LB/HR | 0 | 0 | 0 | 0 | 0 | 0 | 0 | 0 | #N/A | #N/A |
| WATER | LB/HR | 83,597 | 83,597 | 38,409 | 38,409 | 76,838 | 76,838 | 39,373 | 39,373 | #N/A | #N/A |
| ETHANE | LB/HR | 0 | 0 | 0 | 0 | 0 | 0 | 0 | 0 | #N/A | #N/A |
| PROPANE | LB/HR | 0 | 0 | 0 | 0 | 0 | 0 | 0 | 0 | #N/A | #N/A |
| BUTANE | LB/HR | 0 | 0 | 0 | 0 | 0 | 0 | 0 | 0 | #N/A | #N/A |
| TOLUENE | LB/HR | 0 | 0 | 0 | 0 | 0 | 0 | 0 | 0 | #N/A | #N/A |
| BENZENE | LB/HR | 0 | 0 | 0 | 0 | 0 | 0 | 0 | 0 | #N/A | #N/A |
| OXYGEN | LB/HR | 0 | 0 | 0 | 0 | 0 | 0 | 0 | 0 | #N/A | #N/A |
| CARBON_DIOXIDE | LB/HR | 0 | 0 | 0 | 0 | 0 | 0 | 0 | 0 | #N/A | #N/A |
| NITROGEN | LB/HR | 0 | 0 | 0 | 0 | 0 | 0 | 0 | 0 | #N/A | #N/A |
| PENTENE | LB/HR | 0 | 0 | 0 | 0 | 0 | 0 | 0 | 0 | #N/A | #N/A |
| DICYCLO-PENTADIENE | LB/HR | 0 | 0 | 0 | 0 | 0 | 0 | 0 | 0 | #N/A | #N/A |
| HEPTENE | LB/HR | 0 | 0 | 0 | 0 | 0 | 0 | 0 | 0 | #N/A | #N/A |
| OCTANE | LB/HR | 0 | 0 | 0 | 0 | 0 | 0 | 0 | 0 | #N/A | #N/A |
| OCTENE | LB/HR | 0 | 0 | 0 | 0 | 0 | 0 | 0 | 0 | #N/A | #N/A |
| NONANE | LB/HR | 0 | 0 | 0 | 0 | 0 | 0 | 0 | 0 | #N/A | #N/A |
| DECANE | LB/HR | 0 | 0 | 0 | 0 | 0 | 0 | 0 | 0 | #N/A | #N/A |
| STYRENE | LB/HR | 0 | 0 | 0 | 0 | 0 | 0 | 0 | 0 | #N/A | #N/A |
| TOTAL | LB/HR | 83,597 | 83,597 | 38,409 | 38,409 | 76,838 | 76,838 | 39,373 | 39,373 | #N/A | #N/A |
| ENTHALPY | BTU/LB | −5,593 | −6,348 | −5,593 | −6,348 | −5,593 | −6,348 | −5,593 | −6,348 | #N/A | #N/A |
| DENSITY | LB/CUFT | 0.90 | 46.62 | 0.90 | 46.62 | 0.90 | 46.62 | 0.90 | 46.62 | #N/A | #N/A |

-continued

| | | | | | | | | | | |
|---|---|---|---|---|---|---|---|---|---|---|
| VOLUMETRIC_FLOW | GPM | 11,612 | 224 | 535 | 103 | 10,673 | 295 | 5,469 | 105 | #N/A #N/A |

| | | STREAM NUMBER | | | | | |
|---|---|---|---|---|---|---|---|
| | | 66 | 68 | 106 | 107 | 108 | 109 |
| TEMPERATURE | DEG F. | 88 | 108 | 212 | 466 | 212 | 466 |
| PRESSURE | PSIA | 50 | 45 | 500 | 495 | 500 | 495 |
| COMPONENTS | | | | | | | |
| HYDROGEN | LB/HR | 0 | 0 | 0 | 0 | 0 | 0 |
| METHANE | LB/HR | 0 | 0 | 0 | 0 | 0 | 0 |
| WATER | LB/HR | 1,170,770 | 1,170,770 | 9,723 | 9,723 | 9,664 | 9,664 |
| ETHANE | LB/HR | 0 | 0 | 0 | 0 | 0 | 0 |
| PROPANE | LB/HR | 0 | 0 | 0 | 0 | 0 | 0 |
| BUTANE | LB/HR | 0 | 0 | 0 | 0 | 0 | 0 |
| TOLUENE | LB/HR | 0 | 0 | 0 | 0 | 0 | 0 |
| BENZENE | LB/HR | 0 | 0 | 0 | 0 | 0 | 0 |
| OXYGEN | LB/HR | 0 | 0 | 0 | 0 | 0 | 0 |
| CARBON_DIOXIDE | LB/HR | 0 | 0 | 0 | 0 | 0 | 0 |
| NITROGEN | LB/HR | 0 | 0 | 0 | 0 | 0 | 0 |
| PENTENE | LB/HR | 0 | 0 | 0 | 0 | 0 | 0 |
| DICYCLO-PENTADIENE | LB/HR | 0 | 0 | 0 | 0 | 0 | 0 |
| HEPTENE | LB/HR | 0 | 0 | 0 | 0 | 0 | 0 |
| OCTANE | LB/HR | 0 | 0 | 0 | 0 | 0 | 0 |
| OCTENE | LB/HR | 0 | 0 | 0 | 0 | 0 | 0 |
| NONANE | LB/HR | 0 | 0 | 0 | 0 | 0 | 0 |
| DECANE | LB/HR | 0 | 0 | 0 | 0 | 0 | 0 |
| STYRENE | LB/HR | 0 | 0 | 0 | 0 | 0 | 0 |
| TOTAL | LB/HR | 1,170,770 | 1,170,770 | 9,723 | 9,723 | 9,664 | 9,664 |
| ENTHALPY | BTU/LB | −6,807 | −6,789 | −6,683 | −5,593 | −6,683 | −5,593 |
| DENSITY | LB/CUFT | 61.68 | 61.00 | 57.31 | 0.90 | 57.31 | 0.90 |
| VOLUMETRIC_FLOW | GPM | 2,366 | 2,393 | 21 | 1,351 | 21 | 1,342 |

| | | STREAM NUMBER | | | | | | | | |
|---|---|---|---|---|---|---|---|---|---|---|
| | | 75 | 76 | 85 | 92 | 93 | 98 | 103 | 104 | 914 |
| TEMPERATURE | DEG F. | 105 | 140 | 140 | 105 | 140 | 105 | 105 | 140 | 128 |
| PRESSURE | PSIA | 15 | 14 | 14 | 15 | 14 | 15 | 15 | 14 | 17 |
| COMPONENTS | | | | | | | | | | |
| HYDROGEN | LB/HR | 0 | 0 | 0 | 0 | 0 | 0 | 0 | 0 | 0 |
| METHANE | LB/HR | 0 | 0 | 0 | 0 | 0 | 0 | 0 | 0 | 0 |
| WATER | LB/HR | 0 | 0 | 0 | 0 | 0 | 0 | 0 | 0 | 0 |
| ETHANE | LB/HR | 0 | 0 | 0 | 0 | 0 | 0 | 0 | 0 | 0 |
| PROPANE | LB/HR | 0 | 0 | 0 | 0 | 0 | 0 | 0 | 0 | 0 |
| BUTANE | LB/HR | 0 | 0 | 0 | 0 | 0 | 0 | 0 | 0 | 0 |
| TOLUENE | LB/HR | 0 | 0 | 0 | 0 | 0 | 0 | 0 | 0 | 0 |
| BENZENE | LB/HR | 0 | 0 | 0 | 0 | 0 | 0 | 0 | 0 | 0 |
| OXYGEN | LB/HR | 60,131 | 374,661 | 60,131 | 1,430,390 | 1,430,390 | 374,661 | 712,871 | 712,871 | 7,113 |
| CARBON_DIOXIDE | LB/HR | 0 | 0 | 0 | 0 | 0 | 0 | 0 | 0 | 0 |
| NITROGEN | LB/HR | 226,205 | 1,409,440 | 226,205 | 5,381,000 | 5,381,000 | 1,409,440 | 2,681,750 | 2,681,750 | 23,425 |
| PENTENE | LB/HR | 0 | 0 | 0 | 0 | 0 | 0 | 0 | 0 | 0 |
| DICYCLO-PENTADIENE | LB/HR | 0 | 0 | 0 | 0 | 0 | 0 | 0 | 0 | 0 |
| HEPTENE | LB/HR | 0 | 0 | 0 | 0 | 0 | 0 | 0 | 0 | 0 |
| OCTANE | LB/HR | 0 | 0 | 0 | 0 | 0 | 0 | 0 | 0 | 0 |
| OCTENE | LB/HR | 0 | 0 | 0 | 0 | 0 | 0 | 0 | 0 | 0 |
| NONANE | LB/HR | 0 | 0 | 0 | 0 | 0 | 0 | 0 | 0 | 0 |
| DECANE | LB/HR | 0 | 0 | 0 | 0 | 0 | 0 | 0 | 0 | 0 |
| STYRENE | LB/HR | 0 | 0 | 0 | 0 | 0 | 0 | 0 | 0 | 0 |
| TOTAL | LB/HR | 286,336 | 1,784,100 | 286,336 | 6,811,300 | 6,811,300 | 1,784,100 | 3,394,620 | 3,394,620 | 30,538 |
| ENTHALPY | BTU/LB | −7 | 15 | 15 | 7 | 15 | 7 | 7 | 15 | 12 |
| DENSITY | LB/CUFT | 0.07 | 0.06 | 0.06 | 0.07 | 0.06 | 0.07 | 0.07 | 0.06 | 0.08 |
| VOLUMETRIC_FLOW | GPM | 511,580 | 3,470,420 | 556,977 | 12,169,500 | 13,249,400 | 3,187,550 | 6,064,980 | 6,603,180 | 50,391 |

-continued

| | | STREAM NUMBER |
| --- | --- | --- |
| | | 912 |
| TEMPERATURE | DEG F. | 104 |
| PRESSURE | PSIA | 115 |
| COMPONENTS | | |
| HYDROGEN | LB/HR | 0 |
| METHANE | LB/HR | 1,404 |
| WATER | LB/HR | 0 |
| ETHANE | LB/HR | 42 |
| PROPANE | LB/HR | 31 |
| BUTANE | LB/HR | 0 |
| TOLUENE | LB/HR | 0 |
| BENZENE | LB/HR | 0 |
| OXYGEN | LB/HR | 1 |
| CARBON_DIOXIDE | LB/HR | 61 |
| NITROGEN | LB/HR | 45 |
| PENTENE | LB/HR | 0 |
| DICYCLOPENTADIENE | LB/HR | 0 |
| HEPTENE | LB/HR | 0 |
| OCTANE | LB/HR | 0 |
| OCTENE | LB/HR | 0 |
| NONANE | LB/HR | 0 |
| DECANE | LB/HR | 0 |
| STYRENE | LB/HR | 0 |
| TOTAL | LB/HR | 1,585 |
| ENTHALPY | BTU/LB | −1,955 |
| DENSITY | LB/CUFT | 0.32 |
| VOLUMETRIC_FLOW | GPM | 609 |

While the invention has been illustrated and described in detail in the drawings and foregoing description, the same is to be considered as illustrative and not restrictive in character, it being understood that only exemplary embodiments have been shown and described. All changes, equivalents, and modifications that come within the spirit of the inventions defined by the following claims are desired to be protected. All publications, patents, and patent applications cited in this specification are herein incorporated by reference as if each individual publication, patent, or patent application was specifically and individually indicated to be incorporated by reference and set forth in its entirety herein.

The invention claimed is:

1. A method for the production of mesitylene from an aromatic composition comprising aromatic components including methyl benzenes and $C_2$ and/or higher alkyl benzenes, including ethyl toluene, comprising:
    a. hydrodealkylating the aromatic components to convert the ethyl toluene to ethane and toluene and to convert the $C_2$ and/or higher alkyl benzenes to the corresponding alkanes and dealkylated aromatics while retaining the methyl benzenes;
    b. transalkylating the methyl benzenes to redistribute the methyl groups among the methyl benzenes to form trimethylbenzenes and other methylated benzenes;
    c. isomerizing the trimethylbenzenes to increase the amount of mesitylene in the aromatic composition; and
    d. recovering by distillation a TMB-rich product from the aromatic composition.

2. The method of claim 1 in which said hydrodealkylating is performed in the presence of a suitable hydrodealkylating catalyst, and the transalkylating is performed in the presence of a suitable transalkylating catalyst.

3. The method of claim 1 and which further includes combining elemental hydrogen with the feed stream for hydrodealkylating.

4. The method of claim 3 further includes combining one or more of nitrogen, methane, ethane and propane with the feed stream for hydrodealkylating.

5. The method of claim 1 which includes removing elemental hydrogen, methane, ethane and propane from the dealkylated product and recycling the elemental hydrogen to combine with the feed stream for hydrodealkylating.

6. The method of claim 5 which removed methane is also recycled to combine with the feed stream for hydrodealkylating.

7. The method of claim 1 which further includes introducing into the feed stream supplemental methylated aromatics.

8. The method of claim 7 includes recovering C10 and higher aromatics and recycling them to the feed stream.

9. The method of claim 8 which said recovering C10 and higher aromatics comprises recovering them from the isomerized product.

10. The method of claim 1 which further includes combining supplemental methylated aromatics with the dealkylated product.

11. The method of claim 10 which includes recovering C10 and higher aromatics and recycling them for combining with the dealkylated product for said transalkylating.

12. The method of claim 11 in which said recovering C10 and higher aromatics comprises recovering them from the isomerized product.

13. The method of claim 1 in which said hydrodealkylating and said transalkylating are performed together.

14. The method of claim 1 in which said transalkylating and said isomerizing are performed together separate from said hydrodealkylating.

15. The method of claim 14 in which said hydrodealkylating and said transalkylating/isomerizing are performed at different temperatures.

16. The method of claim 1 in which said hydrodealkylating and said transalkylating are performed separately and at different temperatures.

17. The method of claim 1 and which further includes processing the dealkylated product prior to said isomerizing to recover benzene, toluene and xylene.

18. The method of claim 1 and which further includes processing the isomerized product to recover benzene, toluene and xylene.

19. The method of claim 18 in which said processing the isomerized product comprises processing by distillation.

20. The method of claim 19 in which said processing by distillation provides a BTX component and a TMB component, and in which said recovering a TMB-rich product comprises distilling the TMB component.

21. The method of claim 20 which said recovering a TMB-rich product by distillation provides a C9 depleted component which is recycled to combine with the feed stream.

22. The method of claim 20 in which said recovering a TMB-rich product by distillation provides a C9 depleted component which is recycled to combine with the dealkylated product for said transalkylating.

23. The method of claim 22 which includes removing elemental hydrogen, methane, ethane and propane from the dealkylated product and recycling removed elemental hydrogen to combine with the feed stream for said hydrodealkylating.

24. A method for the production of mesitylene-containing products from a feed stream comprising $C_9$ aromatic components, comprising:
   a. hydrodealkylating the feed stream to a dealkylated product having C2 and higher alkyl groups including ethyl toluene substantially removed from the aromatic components of the feed stream as their corresponding alkanes;
   b. transalkylating the dealkylated product to a transalkylated product having the distribution of methyl groups among the aromatic components of the dealkylated product rearranged;
   c. isomerizing the transalkylated product to increase the amount of mesitylene in the resulting isomerized product;
   d. processing the isomerized product to recover benzene, toluene and xylene, said processing the isomerized product comprising processing by distillation, said processing by distillation providing a BTX component and a TMB component;
   e. recovering a TMB-rich product from the isomerized product, said recovering a TMB-rich product comprising distilling the TMB component, said recovering a TMB-rich product by distillation providing a C9 depleted component; and
   f. recycling the C9 depleted component to combine it with the dealkylated product for said transalkylating, the C9 depleted component being combined with the dealkylated product to provide a methyl to benzene ratio of about 3.0.

25. The method of claim 24 which includes removing elemental hydrogen, methane, ethane and propane from the dealkylated product and recycling removed elemental hydrogen to combine with the feed stream for said hydrodealkylating.

26. The method of claim 1 in which the aromatic components include C7, C8, C9 and C10 alkyl benzenes, and in which said hydrodealkylating yields aromatic components including mono-, di-, tri- and tetra-methyl benzenes, said transalkylating redistributing the methyl groups among the mono-, di-, tri- and tetra methylbenzenes.

27. The method of claim 26 in which the recovered TMB-rich product is treated to prepare a substantially-pure mesitylene product.

28. The method of claim 26 in which said recovering a TMB-rich product is by distillation.

29. The method of claim 28 which the recovered TMB-rich product is treated to prepare a substantially-pure mesitylene product.

30. The method of claim 28 in which said recovering by distillation produces a bottom component including tetramethylbenzene, and in which bottom component including is recycled prior to said transalkylating.

31. The method of claim 27 in which said hydrodealkylating and said transalkylating are performed separately and at different temperatures.

32. The method of claim 26 in which recovered TMB-rich product is treated to prepare a substantially pure mesitylene product.

33. The method of claim 28 which the feed stream includes lower paraffins, which method further including hydrocracking the paraffins.

* * * * *